(12) United States Patent
Becker

(10) Patent No.: US 7,988,613 B2
(45) Date of Patent: Aug. 2, 2011

(54) METHOD AND APPARATUS FOR THE TREATMENT OF PHYSICAL AND MENTAL DISORDERS WITH LOW FREQUENCY, LOW FLUX DENSITY MAGNETIC FIELDS

(76) Inventor: Paul F. Becker, Stuart, FL (US)

( * ) Notice: Subject to any disclaimer, the term of this patent is extended or adjusted under 35 U.S.C. 154(b) by 0 days.

(21) Appl. No.: 12/760,391

(22) Filed: Apr. 14, 2010

(65) Prior Publication Data

US 2010/0298624 A1 Nov. 25, 2010

Related U.S. Application Data

(60) Division of application No. 11/095,612, filed on Apr. 1, 2005, now Pat. No. 7,819,794, which is a continuation-in-part of application No. 10/927,840, filed on Aug. 27, 2004, now Pat. No. 7,276,020, which is a continuation-in-part of application No. 10/278,109, filed on Oct. 21, 2002, now Pat. No. 6,899,667.

(51) Int. Cl.
*A61N 1/00* (2006.01)

(52) U.S. Cl. ............................................. 600/14; 600/26

(58) Field of Classification Search ................ 600/9–15, 600/26–28; 128/897–898; 607/50–51; 336/90, 336/122, 230

See application file for complete search history.

(56) References Cited

U.S. PATENT DOCUMENTS

| | | | |
|---|---|---|---|
| 4,266,533 A | 5/1981 | Ryaby et al. | |
| 4,428,366 A | 1/1984 | Findl et al. | |
| 4,548,208 A | 10/1985 | Niemi | |
| 4,550,714 A | 11/1985 | Talish et al. | |
| 4,587,957 A | 5/1986 | Castel | |
| 4,616,629 A | 10/1986 | Moore | |
| 4,674,482 A | 6/1987 | Waltonen et al. | |
| 4,889,526 A | 12/1989 | Rauscher et al. | |
| 4,940,453 A | 7/1990 | Cadwell | |
| 5,014,699 A | 5/1991 | Pollack et al. | |
| 5,030,196 A | 7/1991 | Inoue | |
| 5,063,912 A * | 11/1991 | Hughes | ............................ 601/47 |
| 5,116,304 A | 5/1992 | Cadwell | |
| 5,192,263 A | 3/1993 | Kraus | |
| 5,195,941 A | 3/1993 | Erickson et al. | |

(Continued)

FOREIGN PATENT DOCUMENTS

EP 018053 5/1986

(Continued)

*Primary Examiner* — John P Lacyk
(74) *Attorney, Agent, or Firm* — Pillsbury Winthrop Shaw Pittman LLP

(57) ABSTRACT

A method and apparatus for generating electromagnetic fields for healing. A device preferably includes a microcontroller and associated memory, a wire coil in electrical communication with a driving circuit that is controlled by the microcontroller in accordance with a program stored in the associated memory, wherein the driving circuit is effective to produce a pulsed DC output having a frequency in the range of about 0-45 Hz, more preferably in the range of 0.5-14.1 Hz and most preferably around 9.6 Hz. A user interface is provided for selecting one of a plurality of modes of operation and a port (e.g., a USB port) is provided to allow the program stored in the associated memory to be modified by way of a computer, memory card or the Internet. In another embodiment, the apparatus takes the form of a medallion that can be worn around a user's neck or strategically placed on a user's body or embedded in other user hardware such as a combat or racing helmet.

33 Claims, 9 Drawing Sheets

U.S. PATENT DOCUMENTS

| | | | | |
|---|---|---|---|---|
| 5,215,633 | A | 6/1993 | Liboff et al. | |
| 5,224,922 | A | 7/1993 | Kurtz | |
| 5,338,286 | A | 8/1994 | Abott et al. | |
| 5,356,368 | A * | 10/1994 | Monroe | 600/28 |
| 5,368,544 | A | 11/1994 | Tran et al. | |
| 5,415,617 | A | 5/1995 | Kraus | |
| 5,441,495 | A | 8/1995 | Liboff et al. | |
| 5,496,258 | A | 3/1996 | Anninos et al. | |
| 5,507,716 | A * | 4/1996 | LaBerge et al. | 600/27 |
| 5,518,495 | A | 5/1996 | Kolt | |
| 5,665,049 | A | 9/1997 | Markoll | |
| 5,669,868 | A | 9/1997 | Markoll | |
| 5,752,911 | A | 5/1998 | Canedo et al. | |
| 5,769,778 | A | 6/1998 | Abrams et al. | |
| 5,769,970 | A | 6/1998 | Robelet et al. | |
| 5,813,970 | A | 9/1998 | Abrams et al. | |
| 5,842,966 | A | 12/1998 | Markoll | |
| 6,048,302 | A | 4/2000 | Markoll | |
| 6,086,525 | A | 7/2000 | Davey et al. | |
| 6,099,459 | A | 8/2000 | Jacobson | |
| 6,123,658 | A | 9/2000 | Schweighofer et al. | |
| 6,132,361 | A | 10/2000 | Epstein et al. | |
| 6,142,927 | A | 11/2000 | Clark | |
| 6,162,166 | A | 12/2000 | Neuwirth | |
| 6,203,486 | B1 | 3/2001 | Miller et al. | |
| 6,210,317 | B1 | 4/2001 | Bonlie | |
| 6,263,878 | B1 | 7/2001 | Litovitz | |
| 6,280,376 | B1 | 8/2001 | Holcomb | |
| 6,425,852 | B1 | 7/2002 | Epstein et al. | |
| 7,179,218 | B2 * | 2/2007 | Raniere | 600/26 |
| 7,520,848 | B2 | 4/2009 | Schneider et al. | |
| 2001/0003799 | A1 | 6/2001 | Boveja | |
| 2002/0103411 | A1 | 8/2002 | Bailey et al. | |

FOREIGN PATENT DOCUMENTS

GB  2219210  12/1989

* cited by examiner

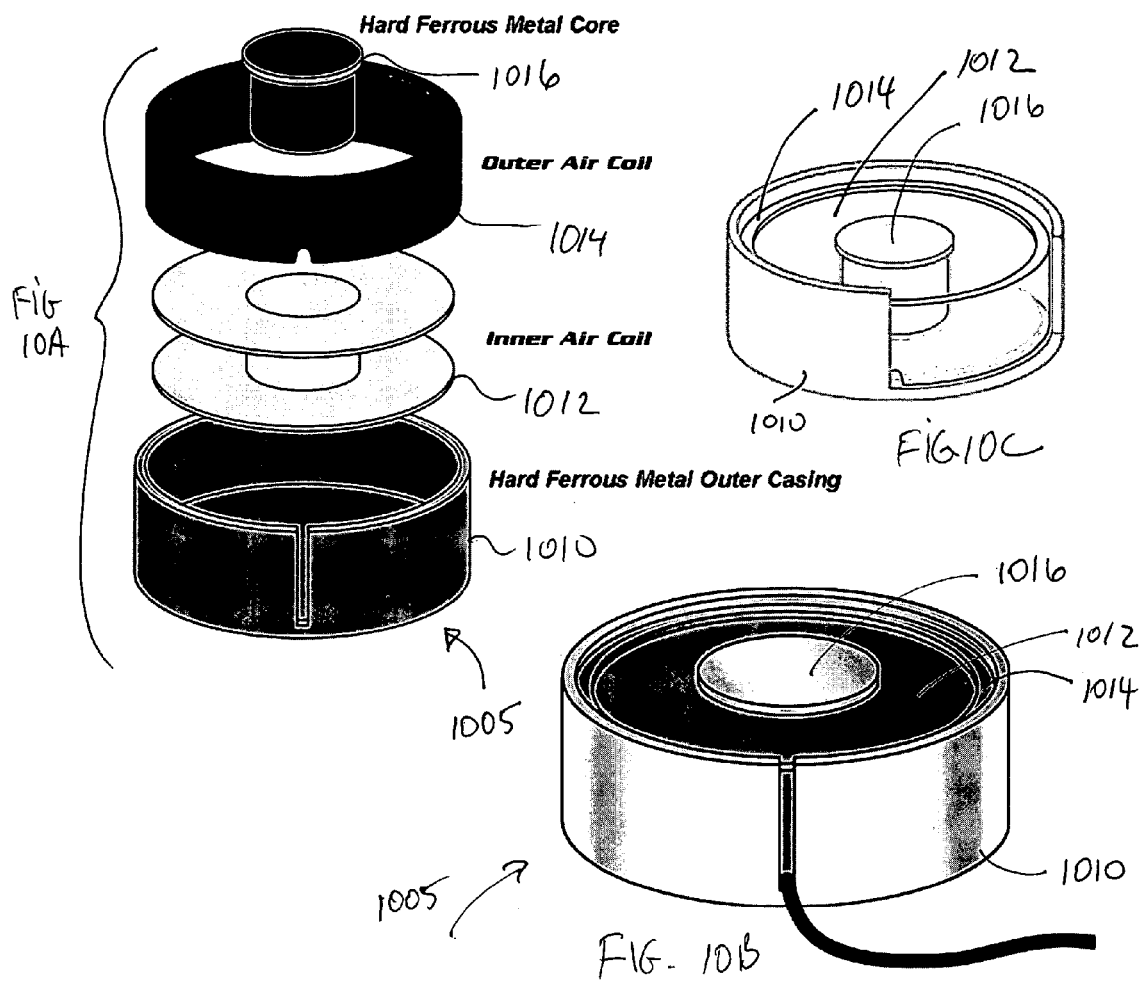

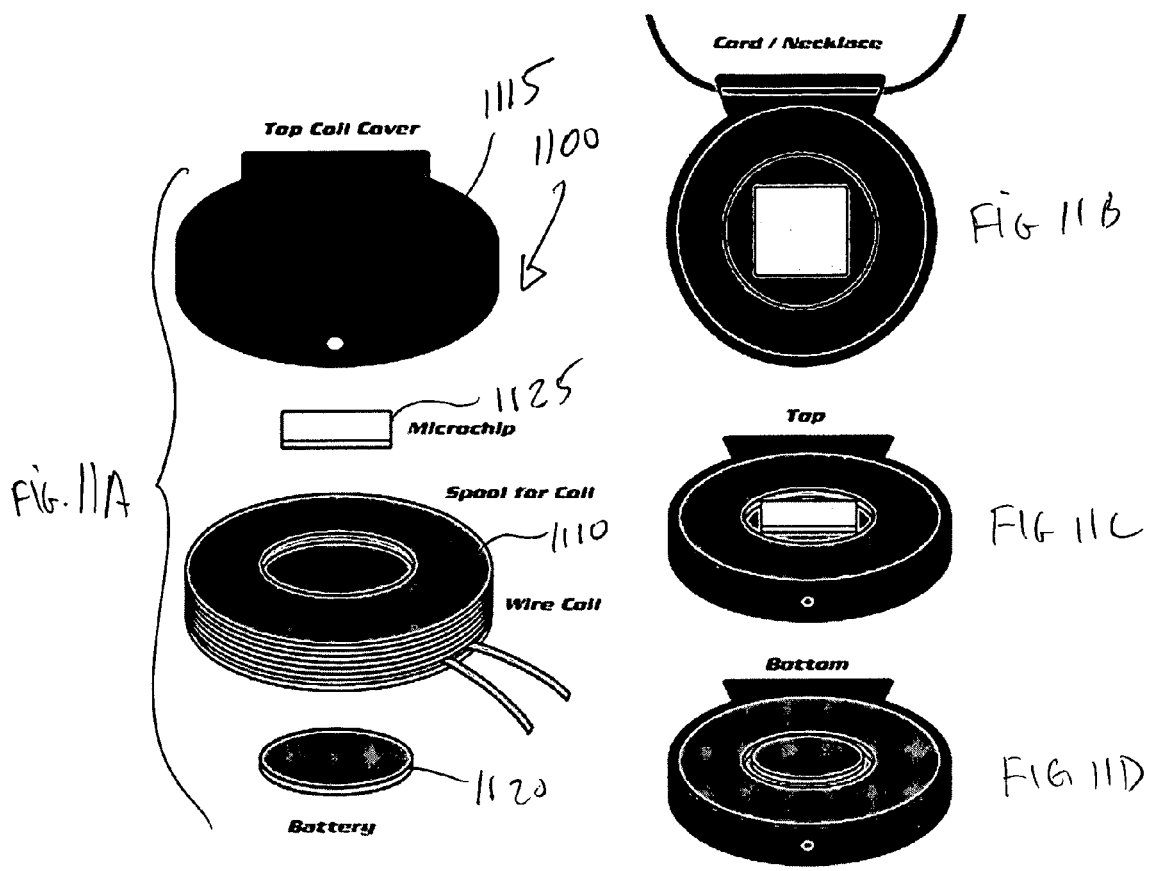

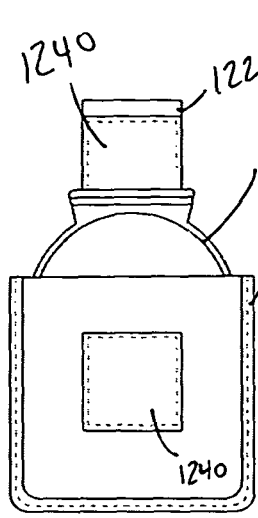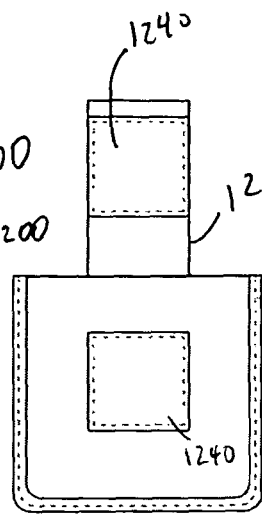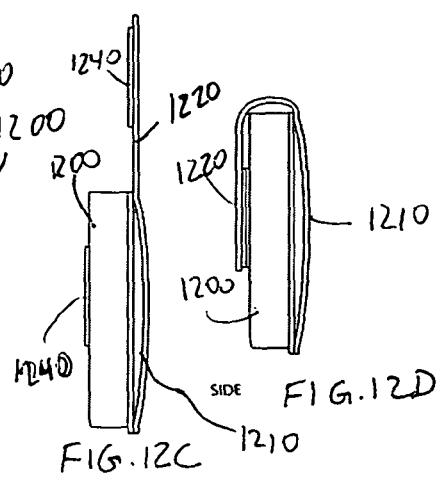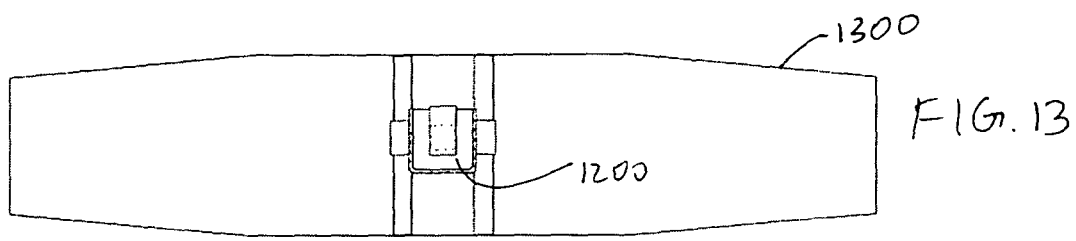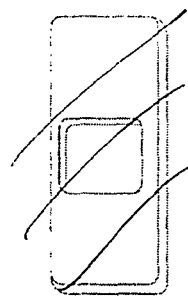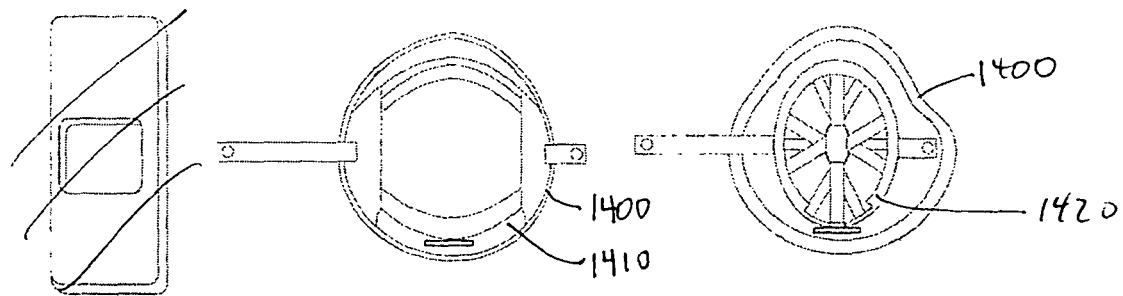

METHOD AND APPARATUS FOR THE TREATMENT OF PHYSICAL AND MENTAL DISORDERS WITH LOW FREQUENCY, LOW FLUX DENSITY MAGNETIC FIELDS

This application is a divisional application of U.S. patent application Ser. No. 11/095,612, filed Apr. 1, 2005 now U.S. Pat. No. 7,819,794, which is a continuation-in-part of U.S. patent application Ser. No. 10/927,840, filed Aug. 27, 2004 now U.S. Pat. No. 7,276,020, which is a continuation-in-part of U.S. patent application Ser. No. 10/278,109, filed Oct. 21, 2002 now U.S. Pat. No. 6,899,667, the contents of each of which are hereby incorporated by reference herein in their entireties.

BACKGROUND

1. Field of the Invention

This invention relates generally to a method and apparatus for the treatment of physical and mental disorders, and, more particularly, to a portable device capable of being operated safely and effectively by patients which produces a time varying, magnetic field having a low frequency and low flux density effective in the treatment of a wide variety of physical and mental disorders.

2. Background of the Invention

Magnetic fields have long been used for the treatment of physical injuries and chronic pain. Early magnetic therapy involved the use of static magnetic fields produced by permanent magnets incorporated into items such as bracelets, belts, back pads, mattress pads and mattresses. It is believed that static magnetic fields have some efficacy in the treatment of broken bones and soft tissue injuries, and tend to promote the circulation of blood as well as relieve stiffness in muscles. The effectiveness of such treatments in human and veterinary applications has been the subject of debate.

More recent attempts to employ the therapeutic effects of magnetic fields have focused on devices which generate an electromagnetic field, and the methods of treatment employing such devices. Although a variety of designs have been proposed in the prior art, electromagnetic devices generally comprise a power supply coupled to a circuit capable of producing an AC or DC output which is transmitted to an inductor coil. One form of inductor coil consists of a number of wire windings wrapped about a coil body with an open or air center, or, alternatively, a ferrous core wrapped with wire windings. In response to the output from the circuit, an electromagnetic field is generated by the inductor coil which is then directed toward the area(s) of the body of a patient to be treated.

In many instances, the circuit of electromagnetic devices produces a pulsed or time-varying output in the shape of a square wave, sine wave, triangular wave or the like. Such output can be at essentially any selected frequency and voltage. A pulsed output from the circuit results in the production of a time-varying or pulsed magnetic field by the inductor coil. If the circuit emits an AC signal, the position of the north and south poles of the resulting magnetic field from the inductor coil changes with each cycle, whereas a DC output produces an electromagnetic field in which the position of the magnetic poles remains constant.

The application of the general concepts of the formation of electromagnetic fields noted above to the treatment of physical and mental disorders has resulted in a widely varying array of devices and treatment methods. Prior art devices operate at completely different ends of the spectrum in terms of field strength and frequency. The predominant approach appears to follow the adage that "more is better." U.S. Pat. Nos. 6,425,852; 6,132,361; 5,813,970 and 5,769,778, for example, teach electromagnetic devices which produce a magnetic field having a flux density in range of up to 10,000 to 20,000 gauss. Devices of this type are used for therapies such as transcranial magnetic brain stimulation for the treatment of neurological and mental disorders. On the other end of the spectrum, devices have been developed for the treatment of various conditions using a magnetic field having a flux density in the range of 10 nanogauss to 10 milligauss, applied at frequencies in the range of 0 to 1000 Hz. See, for example, U.S. Pat. Nos. 6,099,459 and 5,496,258.

There appears to be no consensus whatsoever as to what flux density levels or frequencies should be employed in electromagnetic therapy. Although proposed as a non-invasive alternative to pharmacological and nutritional solutions, it is believed that electromagnetic therapy conducted at the high flux density and/or high frequency levels noted above may, in fact, be harmful whereas treatment at the lower end of the spectrum as suggested in U.S. Pat. No. 6,099,459 will have little, if any, therapeutic effect without extensive technical expertise. None of these treatment methods are reflective of the magnetic field density levels and frequencies which occur naturally within a patient, or are produced naturally within the ionosphere and by the earth.

Other significant limitations of many prior art therapeutic electromagnetic devices is their lack of portability, their complexity and the need for relatively skilled medical personnel to operate them effectively. For example, U.S. Pat. Nos. 6,280,376; 6,099,459; 6,210,317 and application US 2002/0103411 disclose devices which are not portable and require a skilled technician or physician to operate. In order to receive treatment, patients must undertake the time and expense of traveling to the office where the machine is located during normal business hours. Other devices, while they may be more portable, permit a relatively wide range of adjustment of field strength and/or frequency. Allowing patients and practitioners to control these parameters, even with prior instruction, can lead to ineffective or potentially harmful treatment.

BRIEF SUMMARY OF THE INVENTION

It is therefore among the objectives of this invention to provide a method and apparatus for the treatment of physical and mental disorders with electromagnetic therapy which does not require skilled personnel to administer, which is portable, which operates at naturally occurring magnetic field strengths and frequencies, which limits the extent of operating adjustments permitted on the part of a patient or practitioner and which is capable of treating a wide variety of physical and mental disorders in human or animal subjects.

These objectives are accomplished in the instant method and apparatus comprising a circuit adapted to be coupled to a power supply which produces a pulsed DC output, and a magnetic field generating coil coupled to the output of the circuit which is effective to produce a time varying magnetic field having a flux density in the range of about 0.0001 to 90 gauss, and greater, at only specific frequencies which occur naturally within the patient or are naturally occurring terrestrially in the range of about 0 to 45 Hz, and most preferably to no more than about 20 Hz. The coil is positioned at or near the site on the body of the patient to be treated, or, alternatively, beneath the patient's sleeping surface, for a period ranging from about one-half hour to several hours depending upon the condition or method used for treatment.

An important aspect of this invention is predicated upon the concept that naturally occurring magnetic fields, both in terms of flux density and frequency, have beneficial therapeutic effects on a wide variety of physical and mental conditions. It is known that the geomagnetic field strength of the earth is about 0.3 to 0.6 gauss, and that such magnetic field exists terrestrially in the atmosphere and geomagnetically from the earth itself. What has not been recognized prior to the present invention is the beneficial effects of electromagnetic therapy applied at flux density and frequency levels which closely approximate those occurring naturally; further, that these field densities and frequencies when applied nocturnally while sleeping have a cumulative and synergistic effect on many health aspects of the body. It has been found that psychiatric and neurological disorders, central nervous system disorders, tissue damage, orthopedic conditions, wounds, muscle stiffness and a variety of conditions which cause pain and chronic pain all can be safely and effectively treated with a DC, time varying electromagnetic field whose flux density and frequency approximate that which are naturally occurring.

In one embodiment, the device of the instant invention is portable and can be readily and safely operated by patients at home or work without the presence of medical personnel. Such a portable embodiment comprises a housing which contains a circuit operable to produce a pulsed, DC output having a wave form such as square, triangular, sine or the like. In one implementation, the housing is provided with an on/off switch and the frequency of the output is fixed at one level by the circuitry at for instance 9.6 Hz, as this frequency is particularly effective overall. Alternatively, the housing includes an adjustment knob or the like connected to a potentiometer in the circuit for adjustment of the frequency of the output from the circuit. In still another embodiment, a microprocessor is incorporated in the circuitry which is programmable to sequentially vary the output frequency of the circuit to selected frequencies in the range of 0.5 to 45 Hz, and most preferably up to not more than 20.1 Hz, the second most predominant Schumann wave, as the use of higher frequencies may, in some instances, cause stress on the neurological system.

In all embodiments, an inductor coil, e.g., a magnetic field generating coil, is coupled to the output of the circuit. The coil can be in the form of a wire winding about a coil body having an open or air core, or a hard ferrous core, about which the wire is wound. As described below, the two coils are used for different types of treatments in accordance with the method of this invention.

In a preferred implementation, the device is digitally controlled and implemented as a substantially integral "system on a chip" (SOC). Such a design allows for, for example, connectivity to a computer or network via, e.g., a USB or mini USB connector. This connectivity permits a user to download the latest control software for generating the magnetic fields described herein. The SOC design of the present invention also, preferably, allows for more user-defined control through a user interface comprising an LCD display and a plurality of user controls on the device. The user interface may control, for instance, the mode of operation of the device.

One of the operation modes, for instance, is a program designed specifically for deeper more restful sleep. This mode comprises sweeping predetermined frequencies to promote deeper and more restful sleep.

In one implementation, the device incorporates memory for storing music files, which can be played back through a speaker or headphones, in coordination with the type of electromagnetic energy being generated, or independently thereof.

In still another implementation, multiple electromagnets can be connected to a single device such that the magnetic fields generated by the electromagnets are synchronized. Such multiple electromagnets can be use in lieu of two separate devices that might not necessarily generate magnetic fields in synchronicity with each other.

In a slightly different embodiment, the device of the present invention can be configured as a "medallion" to be worn, for example, around one's neck. A device configured in this way preferably includes a rechargeable battery as a power source. A medallion device like this may also be incorporated into clothing, belts and helmets to promote healing, increased metabolism, bone stimulation, brain stimulation, and overall well-being, when positioned in appropriate locations on one's body.

The device of the present invention can also be configured to plug directly into a conventional AC electrical wall socket, or to be mounted, among other places, in a home or vehicle to fill a predetermined space with the therapeutic magnetic fields described herein.

BRIEF DESCRIPTION OF THE DRAWINGS

The structure, operation and advantages of the presently preferred embodiment of this invention will become further apparent upon consideration of the following description, taken in conjunction with the accompanying drawings, wherein:

FIGS. 10A-C show the several components of an exemplary modular electromagnet in accordance with the present invention.

FIGS. 11A-D show the several components of an exemplary medallion in accordance with the present invention.

FIGS. 12A-D show different views of a pouch configured to hold the medallion and be easily attached to the body via a belt, in accordance with the present invention.

FIG. 13 shows the pouch attached to a portion of a conventional back-brace, in accordance with the present invention.

FIGS. 14A-B show how the medallion can be placed into the interior padding of a helmet or onto the interior webbing of a helmet, in accordance with the present invention.

DETAILED DESCRIPTION OF THE INVENTION

Figure 1:
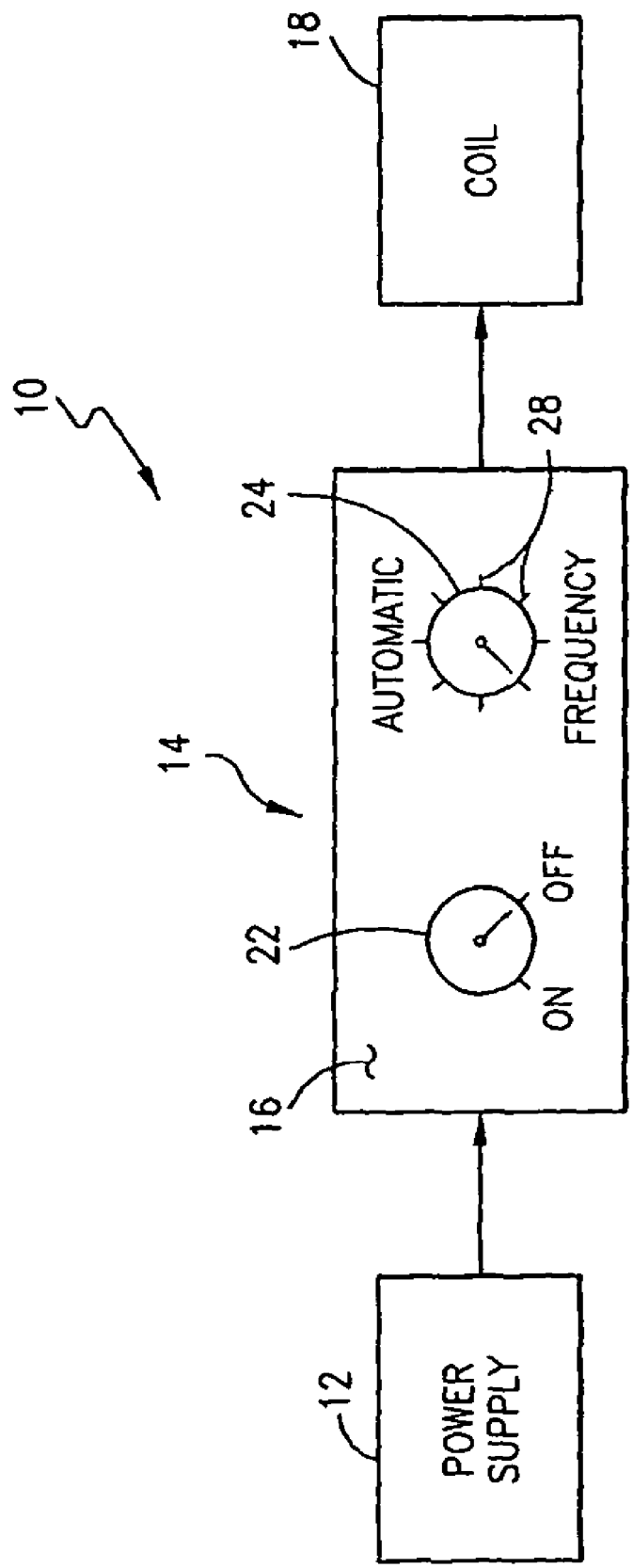
FIG. 1 is schematic illustration of the electromagnetic device of this invention.

Referring now to the drawings, FIG. 1 is a diagrammatic depiction of an electromagnetic device 10 of this invention which comprises a power supply 12, and housing 14 having a control panel 16 and a magnetic field generating or inductor coil 18. The power supply 12 is shown as being coupled to the housing 14, but it should be understood that the power supply could be incorporated within the housing 14 in the form of a battery pack using preferably a rechargeable battery (not shown). Alternatively, the power supply 12 can take the form of a transformer which would plug into a wall socket and step down 120/240 volt supply to voltage for use in the circuit 20 described below in connection with a discussion of FIG. 2.

The housing 14 is shown with a control panel 16 for purposes of illustration. In one embodiment of this invention, the control panel 16 includes only an on/off switch 22 which would turn on the circuit 20 allowing the coil 18 to produce a magnetic field at a predetermined, fixed flux density and frequency. Alternatively, the control panel 16 is provided with a control knob 24 coupled to a potentiometer 26 included within the circuit 20, as described below in connection with a discussion of FIG. 2, to permit variation of the output frequency of the circuit 20, and, hence, the frequency of the magnetic field produced by the coil 18. The control knob 24 may be adjusted manually to selected frequency settings, represented by the radial lines 28 on the control panel 16, or, alternatively, to an "automatic" setting in which a programmable microprocessor 30 within the circuit 20 is activated to sequentially vary the output frequency of the circuit 20, as described below.

Figure 2:
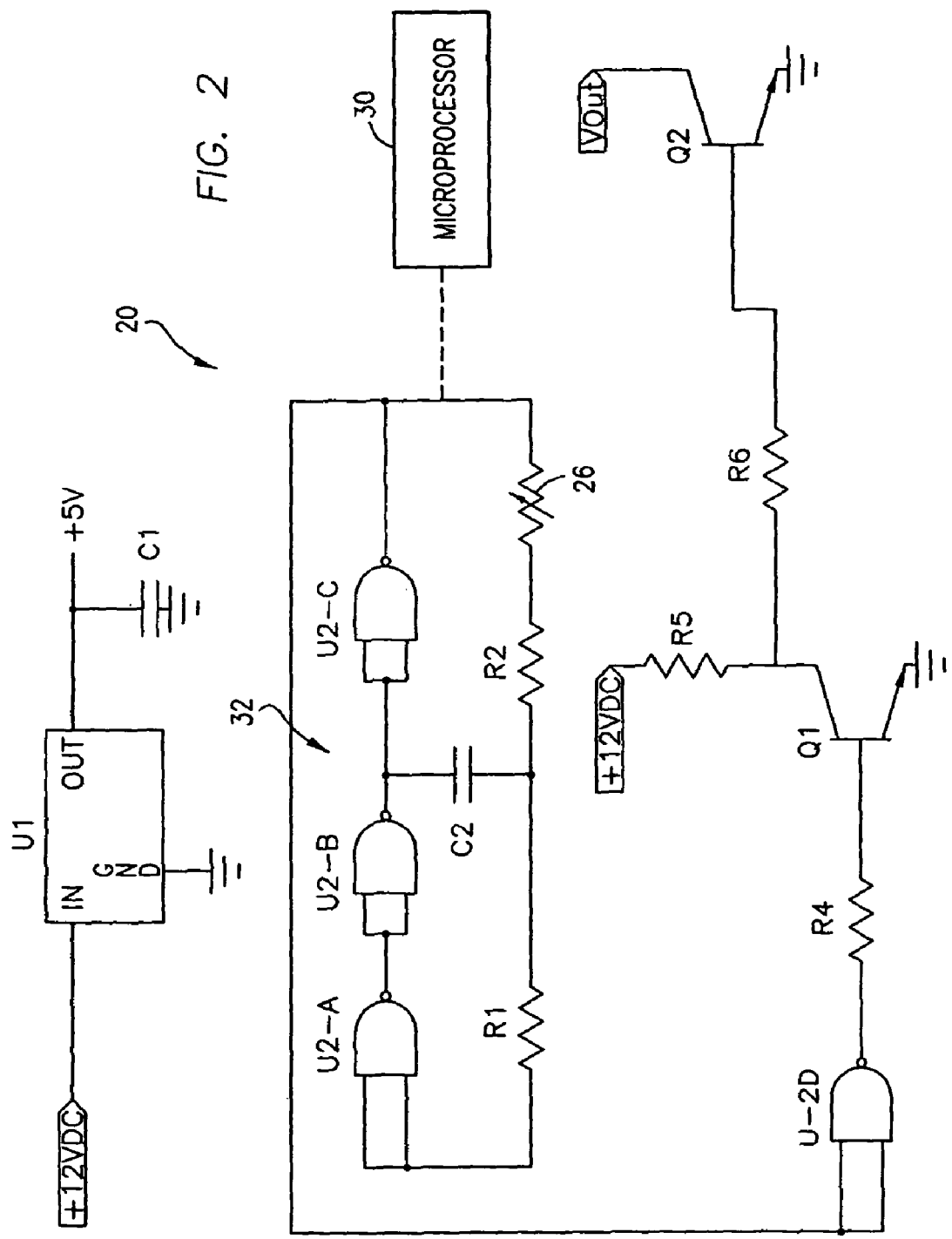
FIG. 2 is a diagram of the circuit of the device in FIG. 1.

Referring now to FIG. 2, the circuit 20 contained within the housing 14 is shown coupled to the power supply 12 which includes an IC voltage regulator U1 and a filter capacitor C1. The power supply 12 provides a voltage output of 5 volts to an astable multivibrator 32 consisting of NAND gates U2-A, U2-B, U2-C, resistors R1 and R2, capacitor C2 and the potentiometer 26. The operating frequency of the astable multivibrator 32 is determined by the values of R1, R2, potentiometer 26 and capacitor C2, which can be varied over a range of 0.5 Hz to 45 Hz (preferably not beyond 20.1 Hz) by operation of the potentiometer 26.

As schematically depicted with a phantom line in FIG. 2, the circuit 20 may optionally include a microprocessor. As noted above, the microprocessor 20 is operative to sequentially vary the frequency output of the astable multivibrator 32. The selected frequencies over which the output is varied are discussed below in connection with the description of a particular treatment method in accordance with this invention.

The signal from the astable multivibrator 32 is input to the NAND gate U2-D which is configured as an inverter. U2-D is connected through resistor R4 to and NPN bipolar junction transistor Q1 configured as an emitter follower to serve as a level shifter, e.g. to convert the signal from 5 volts to the output voltage used in one embodiment or another. Q2 is an NPN bipolar junction transistor which is coupled to Q1 through resistors R5 and R6. It functions to invert the signal from Q1, thus producing a pulsed or time varying DC output signal in the range of 0.5 to 45 Hz, preferably to no more than 20.1 Hz. When the output signal is coupled to the coil 18, a pulsed magnetic field is produced having a flux density in the range of 0.0001 to 90 gauss depending upon the embodiment of the device 10 and the size of the coil 18 which is coupled to the device at a frequency of 0.5 to 45 Hz, and preferably to no more than 20.1 Hz. Since a DC output signal is provided to the coil 18 by the circuit 20, the north and south poles of the resulting magnetic field do not vary in position relative to the coil 18.

Figure 3:
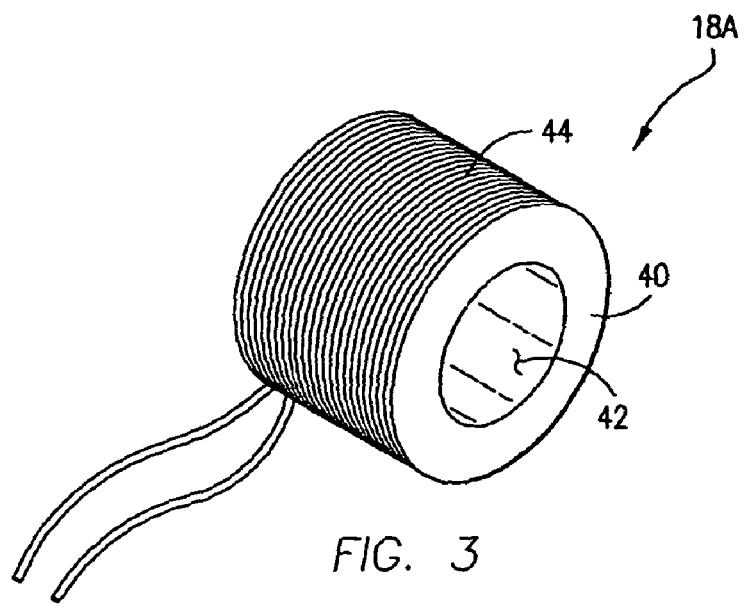
FIG. 3 is a schematic view of an open center coil employed in the subject device.

With reference to FIGS. 3-6, two basic types of a magnetic flux generating coil 18 are shown which are employed in the device 10 of this invention. The magnetic flux generating coil 18A of FIG. 3 includes a coil body 40 with an open center or core 42 around which is wound a wire winding 44. The coil body 40 is schematically depicted in FIG. 3 with a cylindrical shape, but it may take the form of a flat disc in the general shape of a donut. The diameter of the coil body 40 and its thickness can vary, and is chosen to accommodate a particular treatment therapy, as described below.

Figure 4:
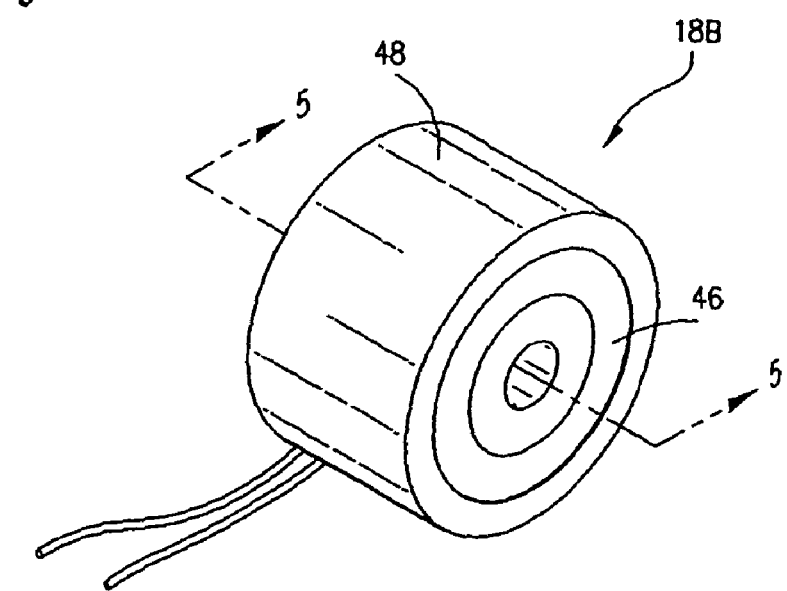
FIG. 4 is a view similar to FIG. 3 of an alternative coil with a hard ferrous center.
Figure 5:
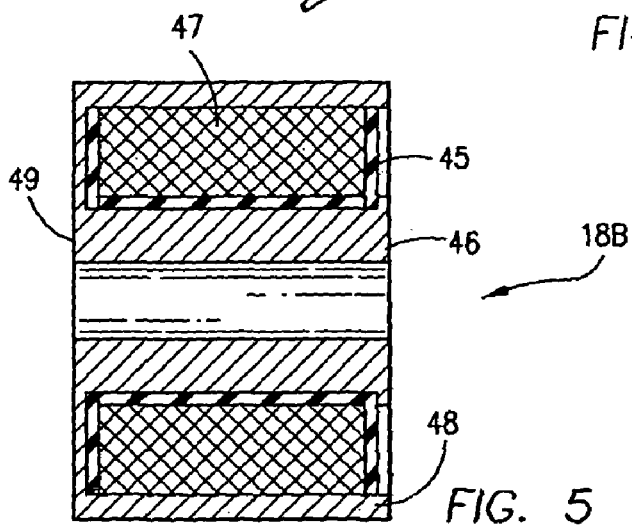
FIG. 5 is a cross sectional view, taken along line 5-5 of FIG. 4.
Figure 6:
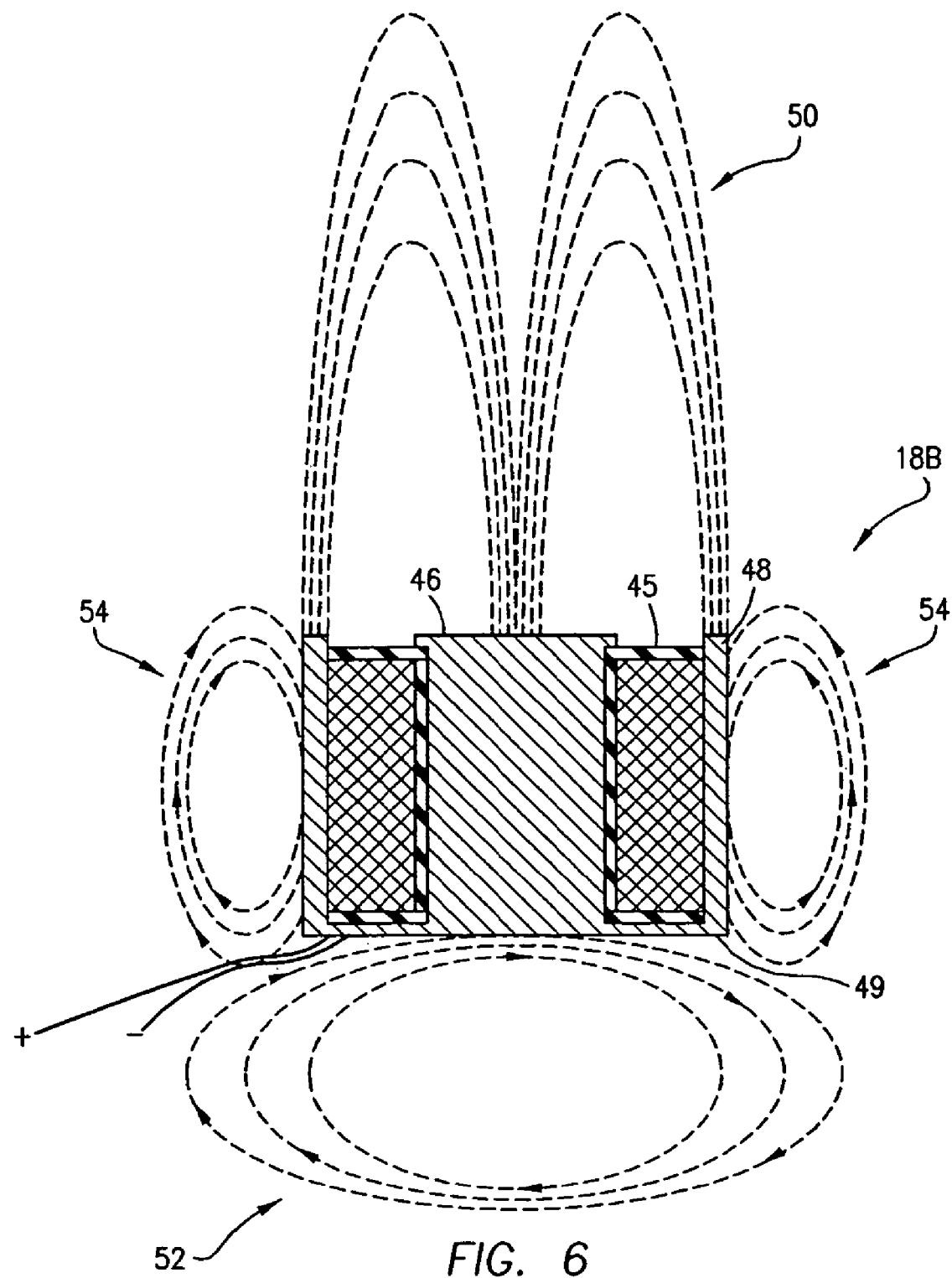
FIG. 6 is a schematic view of the magnetic lines of flux produced by the magnetic flux generating coil of FIG. 4.

The magnetic flux generating coil 18B depicted in FIGS. 4-6 is an electromagnet commercially available from A.P.W. Co. Inc. of Rockaway, N.J. It comprises a core 46 which is made of a hard ferrous material surrounded by a plastic sleeve 45 about which is wrapped a wire winding 47. The wire winding 47, in turn, is received within a metal jacket 48 having an end wall 49. "Hard" ferrous metals are known to possess magnetic memory, that, once energized, are capable of producing a static magnetic field for moments at a time absent any live current through the coil.

The magnetic flux generating coil 18B, in response to the pulsed DC output signal from circuit 20, produces both a time varying magnetic field and a lower amplitude static magnetic field. Because of the magnetic memory possessed by the "hard" ferrous metal, the static magnetic field remains in between the "live" pulsed DC output signal. In response to pulsed DC output signal from circuit 20, coil 18B produces a substantially time varying magnetic field of "north" polarity and simultaneously generates a static magnetic field of "north" polarity in the narrow core which remains after the pulsed DC output signal switches to off; and generates a substantially static "south" polarity magnetic field with a pulsed component out of the opposite pole mounted to the "hard" ferrous jacket. As schematically depicted in FIG. 6, the magnetic lines of flux 50 from the time varying magnetic field with the north polarity project from one end of the hard ferrous core 46. Two magnetic lines of flux 52 and 54 are produced from the substantially static magnetic field with the south polarity. The magnetic lines of flux 52 project from the opposite end of the hard ferrous core 46, and the south magnetic field also travels along the metal jacket 48 forming magnetic lines of flux 54 which project from the same end of the "hard" ferrous core 46 as the time varying, north magnetic field with static component, but in a pattern generally concentric thereto.

The magnetic field with the south polarity is characterized herein as a "substantially static" magnetic field with a time varying "south" polarity component, because the magnetic memory of the comparatively large metal jacket 48, and the frequency of the DC pulses from circuit 20, dissipate into the "hard" ferrous jacket which produce a magnetic field of south polarity having an essentially constant field strength but containing "some" time varying magnetic field of similar "south" polarity. The "time varying" magnetic field projecting from the hard ferrous core 46, on the other hand, has a field strength which increases and decreases with the DC pulse supplied from the circuit 20. Due to the magnetic memory of the hard ferrous core, the time varying magnetic field with a north polarity does not become "zero" in between pulses, but exhibits a static characteristic while the coil 18B is operating, albeit at a lesser field strength than the pulsed field. Consequently, both a pulsed north magnetic field and a lower field strength, static north magnetic field, whose lines of flux are not shown, project from the hard ferrous core 46 of the coil 18B.

The combination of a time varying north magnetic field, a substantially static north magnetic field and a substantially static south magnetic field, all acting in the same direction but with the south magnetic field projecting in concentric relation to the north magnetic fields, provides a beneficial, therapeutic effect when used in accordance with the methods of treatment of this invention. The device 10 of this invention has been successfully employed in treating a number of different conditions. The configuration of the device 10, method of treatment and related case studies for different types of disorders or conditions are discussed in separate sections below.

Psychiatric, Neurological and Central Nervous System Disorders

In one embodiment of the method of this invention, the device 10 is used to apply repetitive transcranial magnetic stimulation ("rTMS") to the back, frontal portion or other areas of the head. It is believed that the application of a pulsed, DC electromagnetic field, at the flux density and frequency ranges noted above and discussed in more detail below, is a novel approach to brain wave entrainment which has the attendant benefits of reducing errant brain wave activity and stimulating certain neurological processes. When applied to the frontal brain regions, rTMS therapy performed with the device 10 herein has an upmodulatory effect on both the mesolimbic and mesostriatal dopaminergic systems. An increase in dopaminergic neurotransmission may contribute to the beneficial effects of rTMS in the treatment of psychiatric and neurological disorders. Further, rTMS performed according to this invention synchronizes the circadian rhythm and neuroendocrine functions of the pineal, hypothalamus and pituitary glands.

The pineal gland, which has been found to be particularly sensitive to magnetic fields, regulates the function of the pituitary, thyroid and adrenal glands through the production of several neurochemical agents. It also affects the central nervous system and immune system via the production of melatonin. Melatonin has been found to be a potent antioxidant and free radical scavenger with anti-aging, antimutagenic and oncostatic properties. In pathologies wherein high production of free radicals is a primary cause of disease, melatonin is protective of mitochondrial damage due to oxidative stress, thereby protecting against impaired mitochondrial production of adenosine tri-phosphate ("ATP"), the fuel that fires all cellular processes. Melatonin is also useful in combating oxidative neurotoxicity which is associated with several acute and chronic neurodegenerative diseases. It has been shown to possess anti-inflammatory effects and reduces tissue destruction during inflammatory reaction. Melatonin attenuates transendothelial cell migration and edema which contribute to tissue damage by reducing the regulation of a variety of proinflammatory cytokines.

In order to perform therapeutic treatment on a selected area of the head, the device 10 is employed with an air core coil 18A positioned proximate the head, e.g. about 5 to 10 centimeters away from the head, beneath a pillow or other padding for comfort. The patient can be placed in a prone or reclined seated position, or lying flat on a surface. In most instances, it is preferable to place the coil 18A at the back of the head, although it may be located proximate any specific area exhibiting symptoms to be treated. The pulsed, DC output from circuit 20 results in a time varying magnetic field from the coil 18A whose north and south poles remain in the same position relative to the coil 18A. With a flux density level at the coil 18A of in the range of about 30 gauss, and the coil 18A positioned at the back of the head beneath a pillow, the flux density at the back of the patient's head is typically on the order of about 1-2 gauss. The flux density at the subthalmic region of the brain is significantly less.

It has also been discovered that certain symptoms respond more favorably to utilization of the solid core "hard" ferrous electromagnet for applying rTMS. Specifically, a majority of Parkinsonians appear to respond more favorably to this "hard" ferrous electromagnet as do those who suffer from acute migraine headache.

In the method of treatment employing rTMS according to this invention, the device 10 is operated using the control knob 24 to vary frequency settings to approximate those of the delta, theta, alpha and beta frequencies of the brain. In the manual mode of operation, the control knob 24 is turned to an initial setting, represented by radial lines 28 on the control panel 16 of housing 14, and then sequentially moved to different settings every 1 to 2 minutes or so. If only one or two of the brain wave segments is to be treated, the control knob 24 is operated accordingly. Alternatively, a microprocessor may be set to the automatic mode of operation in which case the microprocessor 30 functions to sequentially shift between the delta, theta, alpha and beta frequency segments at timed intervals.

It is generally accepted that the frequency segments of the brain range in frequency from about 0.5 to 20 Hz, unless in a stressed or anxious condition, with the delta segment being in the range of about 0 to 3 Hz, the theta segment about 3 to 8 Hz, the alpha segment about 8 to 12 Hz and the beta segment about 12 to 20 Hz and higher. Respective settings or radial lines 28 on the control panel of housing 14 correspond to specific frequencies within each of these frequency ranges so that each of the delta, theta, alpha and beta segments of the brain can be treated by sequential movement of the control knob 24 to different settings or by operation of the circuit 20 in the microprocessor "automatic" mode. In the presently preferred embodiment, the setting corresponding to the alpha segment frequency range of about 8 to 12 Hz is specifically set at 9.6 Hz.

Solar particles trapped in the ionosphere of the earth are found to resonate at frequencies of about 7.83, 14.1, 20.3, 26.4, 31.32, 39 and 45 Hz, known as the Schumann wave frequencies. A principle objective of this invention is to provide a therapeutic magnetic field at a flux density and frequencies substantially the same as those occurring in nature. Accordingly, the microprocessor 30 may also be programmed to cause the circuit 20 to produce an output signal which varies in frequency corresponding to the Schumann wave frequencies. The magnetic field produced by coils 18A and 18B at such frequencies is believed to be beneficial for the treatment of pain and other conditions while the lower three frequencies double as rTMS brain wave entrainment frequencies.

Research has shown that rTMS performed in accordance with the method of this invention is effective at reducing symptoms of central nervous system disorders, including, without limitation, Alzheimer's disease, epilepsy, seizure disorders in general, multiple sclerosis, depression, Parkinson's disease, schizophrenia and dementias of various etiologies, migraine headache, cluster headache, recurrent headache syndromes in general, severe pre-menstrual and pre-menopausal syndromes, attention deficit disorders, age-related cognitive and motor deficits, optic nerve atrophy and degenerative diseases of the retina. Improvements will also be realized in cognitive and motor functions including spatial orientations, sense of balance, improved mobility, memory, alertness, organizational skills and problem solving abilities; improved mood or decreased depression and anxiety; increased endurance, strength and stamina; and improved hand-eye coordination.

A number of subjects have been treated with the device 10 employing the method described herein, as follows.

Case 1: A 74 year old fully medicated male was diagnosed 15 years ago with Parkinson's disease, and experienced mild consistent tremor in the right hand, erratic sleep with many sleepless nights, weakness in the arms and legs and moderate to pronounced balance deficit. One 45 minute rTMS session with the inductor coil 18A set to deliver magnetic flux density of about 0.6 gauss at 9.6 Hz applied to back of head resulted in dramatic improvement in balance, speaking volume, strength, motor coordination and sleep patterns. The tremor was reduced significantly to nearly nonexistent. The subject continued the same self-administered treatment, two to three days a week, and over a three month period the subject slowly lost about 25% of the initial benefit at 9.6 Hz. At this point, rTMS sessions employing the coil 18A producing a flux density of 0.6 gauss but sequentially set at delta, theta, alpha and beta frequencies was initiated and applied during rest in bed with the coil 18A placed under 2 pillows behind the back of head delivering approximately 0.2 gauss to the subthalmic region of the brain. Such treatments applied 2-3 times weekly have produced steady improvement in all aspects of motor and cognitive deficit to a new baseline high.

Case 2: A 76 year old, unmedicated male was diagnosed with Parkinson's disease in 1985. The subject experienced severe tremor in both hands, nighttime anxiety requiring several over-the-counter or prescription sleep aids nightly for the past three years, pain in neck, arms, legs and hands, and weakness in the hands, arms and legs. After one 45 minute rTMS session using the coil 18A of this invention operated to produced a 0.6 gauss magnetic flux density at 9.6 Hz applied to back of head under two pillows, the tremor was reduced by about 50%, the subject slept well with no sleeping pills, anxiety was reduced to near nonexistent, mobility in the hands increased dramatically, overall pain was reduced to 25% of baseline and strength in the hips and legs improved by about 30%. This same therapy was continued three times per week for eight weeks, and the subject continued to sleep well with no sleep medication, the tremor in both hands was reduced to about 15% of baseline and strength in the legs and hands further improved. At week 9, rTMS brain wave sessions using the coil 18A operated to produce a 0.6 gauss flux density at delta, theta, alpha and beta frequencies were initiated but applied during rest in bed with the coil 18A placed under the mattress in alignment with the patient's head and yielding approximately 0.1 gauss to the subthalmic region of the brain. Self-administered magnetic brain-wave entrainment for 30 minutes each evening has resulted in further tremor reduction to 5-10% of baseline and reduced incidence of tremor episodes, better mood, clarity of thinking and further improvement in strength and further reduction of overall pain.

Case 3: A 32 year old female, diagnosed with multiple sclerosis in 1992, exhibited symptoms including an erratic signature, poor mood with mild depression, very little energy and the need to walk with a walker. After three, one hour rTMS sessions using the coil 18A operated to produce a 0.7 gauss flux density magnetic field at delta, theta, alpha and beta frequencies, applied to the back of the head, the subject's mood improved, her facial expressions were more animated with better color in the face, her sleep improved with no need for sleep aids, her signature has improved to nearly normal and her leg strength and stamina have improved about 20%.

Case 4: One of two 40 year old identical twin sisters was administered a 45 minute, rTMS session using the coil 18A operated to produce a 0.7 gauss flux density magnetic field at delta, theta, alpha and beta frequencies applied to back of head under two pillows twice weekly. Although both sisters have been diagnosed as border-line schizophrenics, the twin receiving treatment experienced improvements in mood, motivation and well-being, even while engaged in rigorous academic endeavors which, in the past, had exacerbated her symptoms. Their mother has noted a significant improvement in the treated twin, i.e., the schizophrenic episodes have diminished significantly despite her rigorous academic endeavors, while the other twin remains the same.

Case 5: A 62 year old male had been experiencing balance deficit. Two 45 minute sessions using the coil 18A operated to produce a magnetic field with a flux density of 0.6 gauss at 9.6 Hz, located at the back of the head, corrected the balance deficit by about 80%. The subject has continued self administered therapy once per week and reports balance deficit as nearly nonexistent. The subject also reports sleeping sounder and feeling better overall.

Case 6: A 72 year old female had been experiencing balance deficit when ballroom dancing. One 45 minute rTMS session using the coil 18A operated to produce a 0.7 gauss flux density magnetic field set at 9.6 Hz, and applied through one pillow located at the back of head, improved balance significantly while making the subject sleep recognizably better.

Case 6a: A 73 year old male had been experiencing balance deficit when ballroom dancing. One 45 minute rTMS session using the coil 18A operated to produce a magnetic field having a flux density of about 0.7 gauss at 9.6 Hz, and applied through one pillow located at the back of head, improved balance significantly.

Case 7: A 44 year old male experienced balance deficit while walking the seawall behind his property, and while surfing. He also noticed difficulty driving in that he found himself weaving within lanes especially when taking his eyes off of the road even for a couple of seconds. One 45 minute rTMS session using the coil 18A operated to produce a magnetic field having a flux density of about 0.7 gauss at 9.6 Hz, applied to the back of the head, completely eradicated the balance deficit while restoring his driving proficiency especially in regard to not weaving within highway traffic lane lines. After two additional 45 minute rTMS sessions of the same type noted above, the subject's physical endurance/stamina unexpectedly improved by about 25% as measured by specific exercise movements performed to failure.

Case 8: A 52 year old male noticed cognitive deficit relating to balance, coordination and decision making process. One 45 minute rTMS session using the coil 18A operated to produce a 0.6 gauss flux density magnetic field at 9.6 Hz, applied to back of head through a pillow, resulted in significant improvement in balance, hand-eye coordination and thought/decision making processes.

Pain Management and Treatment of Underlying Conditions Causing Pain

It has been found that the device 10 of this invention is useful in the management of pain and the treatment of a variety of conditions which create pain and inflammation, including, without limitation, bone non-union, bone fractures, joint abnormalities and degenerative disorders, spinal or degenerative disk disorders, neuralgia, neuropathy, chronic pelvic pain syndromes, temporomandibular joint disorder ("TMJ"), post-traumatic maxillofacial defects, fibromyalgia, sciatica, spinal cord injuries and resulting neuromuscular deficits, acute pain and inflammation due to arthritis, periarthritis, osteochondrosis, osteoporosis, trauma, chronic ulcers, diabetic neuropathy or circulatory problems, muscle spasms, muscle soreness, muscle stiffness and others. Two types of therapies are performed with the device 10 to treat these conditions, including one with the coil 18A of FIG. 3 and the other with the coil 18B of FIG. 4.

In one presently preferred embodiment, one or more coils 18A are placed beneath the sleeping surface of a patient in general alignment with the head or other area of the body which is experiencing pain or other symptoms to be treated. The coil 18A can be placed under the mattress pad proximal to the injury or under the entire mattress of the sleeping surface. The time varying magnetic field produced by the coil 18A is approximately 30 gauss in the immediate area of the coil 18A, and preferably in the range of about 0.05 to 0.1 gauss at the interface of the patient and the sleeping surface directly above the coil 18A, depending upon the thickness of the mattress pad or mattress. Preferably, the patient is exposed continuously to the magnetic field from the coil 18A for a normal sleeping period, e.g. 6 to 8 hours per treatment. The treatment is appropriate for rTMS or to stimulate a wide variety of healing mechanisms in damaged tissues.

Sleeping in the DC, time varying magnetic field generated by the device 10 of this invention is believed to induce the repair and regeneration of many types of physical and neurological injuries, to enhance the efficiency of cellular processes including promoting the body's synthesis of adenosine tri-phosphate and to enhance the blood's ability to carry oxygen. This increases the supply of oxygen and nutrients via the vascular system, improves the removal of waste through the lymphatic system and helps to rebalance the distribution of ions across the cell membrane. Healthy cells in tissue have a membrane potential difference between the inner and outer membrane causing a steady flow of ions through its pores. In a damaged cell, the potential is raised and an increased sodium flow occurs. As a result, interstitial fluid is attracted to the area, resulting in swelling and edema. The application of DC pulsed magnetic fields to damaged cells in accordance with the method of this invention accelerates the reestablishment of normal potentials thus tending to increase the rate of healing while reducing swelling, bruising and inflammation.

The coil 18A, or any array of coils 18A, or in cases of acute injury where coil 18B is employed at night proximal to injury, produce homogenous magnetic waves which expand and collapse radially therefrom with little or no eddy currents to the subject being treated. If two persons sleeping in the same bed are to be treated simultaneously, the coils are preferably located at least 3 feet apart and beneath each of the two sleeping subjects to avoid or reduce the intensity of the intersection of the magnetic field produced by each coil.

Case 1: A 44 year old male has been rehabilitating rotator cuff and ligaments in and around hid left shoulder for over 15 years since dislocating the shoulder 3 times during a period of 10 years in sports-related incidents. A coil 18A was placed between the mattress and box spring of the subject's bed, in substantial alignment with the shoulder area, while sleeping. The coil 18A was operated to produce a magnetic field having a flux density of about 0.7 gauss in the area of the coil 18A, and about 0.01 to 0.05 gauss as measured in the area where the subject laid on the bed, at a frequency of 9.6 Hz. After 4 to 5 nights, the constant pain in the shoulder previously experienced by the subject had ended and the subject slept better without being awakened by shoulder pain during the night. By the tenth day, the subject was able to lift weights without the ringing and shooting pain, or the clicking and crunching noises, which he had previously experienced in the left rotator cuff and shoulder ligaments especially while the shoulder was under structural load. Significant improvements in strength and stamina of his upper body during such workouts were evident. The subject has subsequently surfed a number of times and noticed a reduction of all post-session shoulder pain, back pain and neck to nonexistent levels.

Case 2: A 54 year old female complained of attention deficit, a sleep disorder which caused her to awaken at 6 a.m. regardless of what time she went to bed, and persistent weaving in and out of highway lanes while driving. The subject arranged a coil 18A between the mattress and box spring of her bed in general alignment with the back of the head, neck and shoulder area. The coil 18A was operated to produce a magnetic field having a flux density of about 0.7 gauss in the area of the coil 18A, and about 0.01 to 0.05 gauss as measured in the area where the subject's head and neck rested on the bed, at a frequency of 9.6 Hz. After two successive nights of all night therapy, during which time the subject slept deeply for 7 hours, the patient felt noticeably calmer, more focused and she slept better and for longer periods of time. The subject is more comfortable driving and can now take her eyes off of road momentarily without swerving nor is she weaving within lanes. The subject has also in the past suffered from 1-2 migraine headache episodes per month which generally lasted for 2-3 days. The subject reports that upon continued use of the device 10 for 1-3 nights per week, the incidence and severity of migraines have been reduced by at least 80%.

Case 3: A 52 year old male has experienced arthritic pain, rotator cuff, neck and back pain for nearly 10 years. Surfing and spear-fishing significantly exacerbates those symptoms. The subject arranged a coil 18A between the mattress and box spring of his bed in general alignment with the back of the head, neck and shoulder area. The coil 18A was operated to produce a magnetic field having a flux density of about 0.7 gauss in the area of the coil 18A, and about 0.01 to 0.05 gauss as measured in the area where the subject's head and neck rested on the bed, at a frequency of 9.6 Hz. After two all night sessions, the subject experienced approximately a 98% decrease in overall pain which lasted for nearly a week with no additional therapy. Surfing sessions increased from 1 hour to up to 3 hours yet pain remained nearly completely relieved for about one week. Subsequently, the subject reported three weeks later that his overall pain was still only 25% of baseline.

Case 4: A husband suffering from lower back pain, who had 4 back operations in which pins and plates were implanted and who, at time, would rely on a cane for assistance walking, and his wife suffering from tendonitis/bursitis of the elbow and previously wearing an elbow support constantly for 6 months, have been sleeping on a mattress under which a coil 18A was positioned in approximately the center of the bed under the husband's side. The coil 18A was operated to produce a magnetic field having a flux density of about 0.7 gauss in the area of the coil 18A, and about 0.01 to 0.05 gauss as measured in the area where the subjects laid on the bed, at a frequency of 9.6 Hz. They report excellent sleep, the wife remains pain free while the husband has been able to take less-potent, non-habit forming pain medication with further reduction of pain, resulting in increased mobility and no further need for his cane. Husband/wife report wife's migraine episodes have been nearly completely ameliorated since night-time therapy was initiated 6 weeks ago.

Case 5: A husband and wife each 40 years old, initiated sleeping upon coil 18A two days prior to onset of the wife's menstrual cycle. The wife had experienced severe menstrual symptoms for 20 years, and over the previous 18 months such menstrual symptoms worsened due presumably to the onset of menopause. At times, should would be completely debilitated with cramps and migraine headache requiring her for the past several months to take 1-2 days off from work at a time. Her menstrual cycle passed with no migraine headache and minor cramping for the first time in over 20 years.

Case 6: A 62 year old woman experienced knee pain subsequent to knee replacement surgery, resulting in restless sleep. Therapy was initiated by sleeping upon coil 18A for two nights after which time the subject reported better sleep with a 10% reduction in pain. The woman's 10 year old dog which sleeps with her on the bed ceased limping from its recently mended, broken leg.

An alternative method of treatment according to this invention for the management of pain and the treatment of the acute underlying conditions which generate pain, employs the coil 18B depicted in FIG. 4 as part of the device 10. In this embodiment, the coil 18B is placed immediately adjacent the affected areas of the body, i.e., at the location where the pain originates, where the pain is referred, and/or where the condition to be treated is located. Additionally, as noted in case study #15 below, the coil 18B may be located under a sleeping surface as in the treatment method employing the open core coil 18A described above.

Preferably, the patient lies or sits in a comfortable position, with the coil 18B positioned as noted above. Care must be taken to align the center of the electromagnet (North pole) directly with the damaged tissue or pain emanation point so that outer ring (South pole) will be surrounding the adjacent area. The time varying magnetic field produced by the coil 18B has a flux density on the order of about 90 gauss at the surface at frequencies preferably in the range of 8-11 Hz, and most preferably at 9.6 which is the pulsed component of the geomagnetic field. Coil 18B creates a strong bi-polar field gradient in the area of application with the damaged tissues being polarized to North and the surrounding, healthy tissue polarized to South. Coil 18B also is composed of hard ferrous metal so that the area is simultaneously exposed to an oscillating and a static magnetic field. The combination of these three factors—frequency, concentric circle relationship of North and South poles and simultaneous exposure to pulsed and static magnetic fields—results in far more profound healing than any method and system available in the prior art. The duration of the treatment is normally 30 to 60 minutes per session, with the number and frequency of the sessions depending upon the severity of the pain or condition, and the results experienced by the patient. The coil 18B may be moved during the session, as desired, e.g., from the area where the pain is being produced to the area where the pain is referred and visa versa. In most instances, it is preferable to position the coil 18B directly over the pain emanation point initially for about 20-45 minutes, and then move the coil 18B at 5-10 minute intervals to other affected areas such as surrounding nerves, muscles or ligaments.

Case 1: A 39 year old female experienced pain in the hip and thigh area due to severe bone/tissue trauma to her left leg in a motorcycle accident 5 years prior. The pain has been recurrent and worsens during changes in weather. The coil 18B was placed in contact with the body over the pain emanation point(s), for one session of about 30 minutes in duration, and operated to produce a magnetic field having a flux density of about 0.7 gauss at 9.6 Hz. The pain was completely eradicated with no further treatment necessary, even though several frontal systems visited the area during the subsequent 4 weeks.

Case 2: A 25 year old male suffered severe trauma to the neck and spine due to a motorcycle accident, resulting in swelling of the spinal cord and loss of all sensation from the chest down. The subject has been confined to a wheelchair with no pain syndromes. The coil 18B was placed in direct contact with the neck, back, hips, knees and feet for approximately 10 minutes each at approximately equal intervals over a one hour period, and operated to produce a magnetic field having a flux density of about 0.9 gauss at 9.6 Hz. During therapy, the subject reported sensations similar to bugs crawling up and down his legs, which was the first sensation the subject had felt below his chest since his accident. Four days post therapy, the patient reported that sensation had partially returned to left calf muscle and hip. Four weeks later the subject reported that he can still feel the touch of a finger to his right calf and hip.

Case 3: A 29 year old female experienced severe TMJ for 3 years involving her neck and muscles of the face. On the morning of the first therapy session, the subject advised she was considering surgery because the pain was unbearable and nothing had relieved or stopped its progression for nearly 3 years. The coil 18B was placed in direct contact with the right side of the patient's neck, first while laying on her back and then her side for approximately one hour, and operated to produce a magnetic field having a flux density of about 0.9 gauss at 9.6 Hz. The subject fell asleep during the therapy on the neck and when she awoke, she was able to open her mouth wide for the first time in over 8 months. Mobility in the neck area improved 90% on her right side, about 70% on her left side and overall pain was reduced by 85-90% from pre-therapy levels.

Case 4: A 38 year old female has been diagnosed with fibromyalgia, which during flare ups, prevent the subject from raising her right elbow above shoulder level. During a recent flare-up while lying prone on her back, the coil 18B was placed in contact with the intersection of the right trapezius muscle and shoulder for 45 minutes, centered over the spine between the shoulders for 10 minutes and then placed at the lumbar region of the spine for 10 minutes. The coil 18B was operated to produce a magnetic field having a flux density of about 0.9 gauss at 9.6 Hz. Upon sitting upright, the subject was able to make full rotation of right arm with no pain, mobility in neck improved by 80-90% and pain in the neck decreased about 85%. The subject's massage therapist confirmed spasms in neck were reduced by 50% immediately after completion of therapy.

Case 5: A 68 year old female was treated complaining of chronic sciatica in right leg. After 15 minutes of therapy with the coil 18B placed at the point where the pain emanated, the discomfort was reduced by about 60%. Massage therapist confirmed spasms in the gluteus maximus muscle were reduced by 30%. The coil 18B was operated to produce a magnetic field having a flux density of about 0.9 gauss at 9.6 Hz.

Case 6: A 28 year old male athlete has experienced lower back pain for several years due to sports activities, and the condition was exacerbated prior to therapy from to three hours of strenuous surfing in sizable waves and strong currents. The coil 18B was placed in direct contact with the back over a one hour period, and operated to produce a magnetic field having a flux density of about 0.9 gauss at 9.6 Hz. The treatment resulted in nearly complete resolution of pain and associated stiffness. On the following morning, the subject played tennis for 2 hours and reported that the back felt much better upon waking, and the relief remained even after playing tennis. Nearly four weeks post-therapy, the subject reports his back pain is still reduced despite surfing several hours twice weekly and playing tennis at least twice weekly.

Case 7: A 54 year old female complained of severe pain in her feet due to ill fitting shoes worn while traveling and hiking through Alaska. The pain syndrome lasted 8 weeks even after taking cortisone shots beginning at week 7. One eight hour therapy session was performed during sleep with the coil 18B placed in the region of the feet under a mattress pad approximately 8-15 cm from soles of her feet. The coil was operated to produce a magnetic field having a flux density of about 0.9 gauss at 9.6 Hz. A resolution of the pain was obtained with the treatment which did not return after at least 12 weeks subsequent to the therapy.

Case 8: A 42 year old male with a history of several back operations which included metal implants in the lumbar region complained of severe lower back pain for several years requiring the use of a cane at times and the constant use of habit forming prescription pain medications on a daily basis. After an initial 2 hour therapy session with the coil 18B placed in direct contact against the lower back and operating to produce a magnetic field having a flux density of 0.9 gauss set at 9.6 Hz, the subject reported significant relief After 4 therapy sessions of the same duration during a 2 week period, the subject reported tremendous reduction of pain and a significant reduction in his need for pain medications. (See Case Study 4 in previous section).

Case 9: A 40 year old female reported bursitis/tendonitis in her right elbow requiring a brace to be worn most days to reduce pain for several months. After a single 1 hour therapy session in which the coil 18B was placed against the elbow and operated to produce a magnetic field of 0.9 gauss at 9.6 Hz, the subject was pain free for 6 days. Repeated therapy sessions of the same duration for two weeks kept the subject pain free and without need for elbow brace. (See Case Study 4 in previous section).

Case 10: A 40 year old male reported severe lower back pain due to a work related incident. The coil 18B was placed in direct contact with the back over a one hour period, and operated to produce a magnetic field having a flux density of about 0.9 gauss to 9.6 Hz. The subject reported a reduction in pain for 5 days to levels less than experienced in the previous 12 years. He treats himself once per week for several hours while lying on a couch in the same manner noted above, and the pain remains about 70-75% reduced.

Case 11: A 45 year old male reported severe neck pain due to an auto accident, resulting in migraine-like, muscle tension headaches lasting days at a time. During a recent headache episode, the coil 18B was placed in direct contact with the neck over a one hour period, and operated to produce a magnetic field having a flux density of about 0.9 gauss to 9.6 Hz. A complete resolution of the headache episode was obtained.

Case 12: A 60 year old female with a degenerated hip and a candidate for hip replacement experienced moderate back and neck pain with restless sleep. The coil 18B was placed in direct contact with the neck for 45 minutes and lower back, over a 45 minutes during a 90 minute period, and operated to produce a magnetic field having a flux density of about 0.9 gauss at 9.6 Hz. The treatment resulted in nearly complete resolution of pain in neck, back and hip, allowing the patient to sleep. The patient was remarkably pain and medication free for 10 days, and sleep improved to near normal for two weeks.

Case 13: A 49 year old male reported an injury to his hip which occurred during birth, resulting in a crooked walk and in severe hip and knee pain throughout his life. The coil 18B was placed in direct contact with the knee and hip over a 15 minute period, and operated to produce a magnetic field having a flux density of about 0.9 gauss to 9.6 Hz. An 80% reduction of pain was obtained which lasted for 8 days. The same therapy was repeated on two other occasions resulting in a reduction in pain of 75% each time the therapy was repeated. Peak pain during a four week period when therapy was not available was still 50% less than normal.

Case 14: A 70 year old candidate for lumbar fusion, reported severe pain in the lumbar region. The coil 18B was placed in direct contact over the lumbar region for a 45 minute period, and operated to produce a magnetic field having a flux density of about 0.9 gauss to 9.6 Hz. The subject's pain was reduced by about 50% for 48 hours. Two subsequent therapy sessions reduced pain for two days at a time to 50% of baseline.

Case 15: A 59 year old female with a neurodegenerative disease experienced daily moderate to severe pain and weakness in the legs. The coil 18B was placed in direct contact with the legs, feet and knees over a period of three hours, and operated to produce a magnetic field having a flux density of about 0.9 gauss at 9.6 Hz. After a 3 hour self therapy session, the subject experienced a reduction in pain of about 70% and the weakness in her legs was reduced by about 25%. The relief lasted for several days.

Case 16: Two sisters 68 and 69 years old were diagnosed with rheumatoid arthritis over two decades ago, each with progressive inflammatory joint destruction resulting in deformity in the ankles, feet and hands. Each received a single hour of therapy to the base of the spine/lower back. Immediately following therapy, the 69 year old reported overall reduction of pain to 30% of baseline, and the 68 year old reported overall pain reduced to 25% of baseline. Ambulation in both significantly improved.

Case 17: 40 year old male diagnosed with moderate to severe spinal stenosis at C2/C4 utilized the solid core electromagnet through a thin pad directly upon the area for 6 months about 1 hour per day while watching television recently received new MRI which was diagnosed recently as mild to moderate spinal stenosis. Patient is in substantially less pain and is far more active than he has been in years.

Case 18: 41 year old male who suffered a Vioxx-related stroke and was left post event with severe auditory stutter which lasted for two weeks, utilized coil 18B at 90 gauss and 0.5-14.1 Hz upon all quadrants of the head for 30 minutes 2-4 times a day, resulting in complete eradication of the speech deficit within 4 days of initiating treatment.

Although the therapies performed with the coils 18A and 18B have been described separately above, it is contemplated that both may be used by patients as part of an overall treatment regime. For example, a patient may undergo a 30 to 60 minute session with the coil 18B applied directly to pain emanation points followed by treatment with the coil 18A or 18B under the mattress for several hours while sleeping. The beneficial results from such combined therapy are cumulative and synergistic. Effects have been observed including improved quality of sleep that benefits the person's appearance and well being.

Further improved therapeutic results are attainable with an embodiment of the invention as depicted in FIGS. 7-11D. These embodiments exploit the benefits of miniaturization available with present day electronics. Here, substantially all of the functionality described previously, in addition to other features, are all provided as a single "system on a chip" (SOC), which is packaged as shown, for example, in FIG. 7. Such miniaturization results in, among other things, improved energy efficiency (little heat generation) and extremely accurate frequency control (up to 0.01 Hz).

Figure 8:
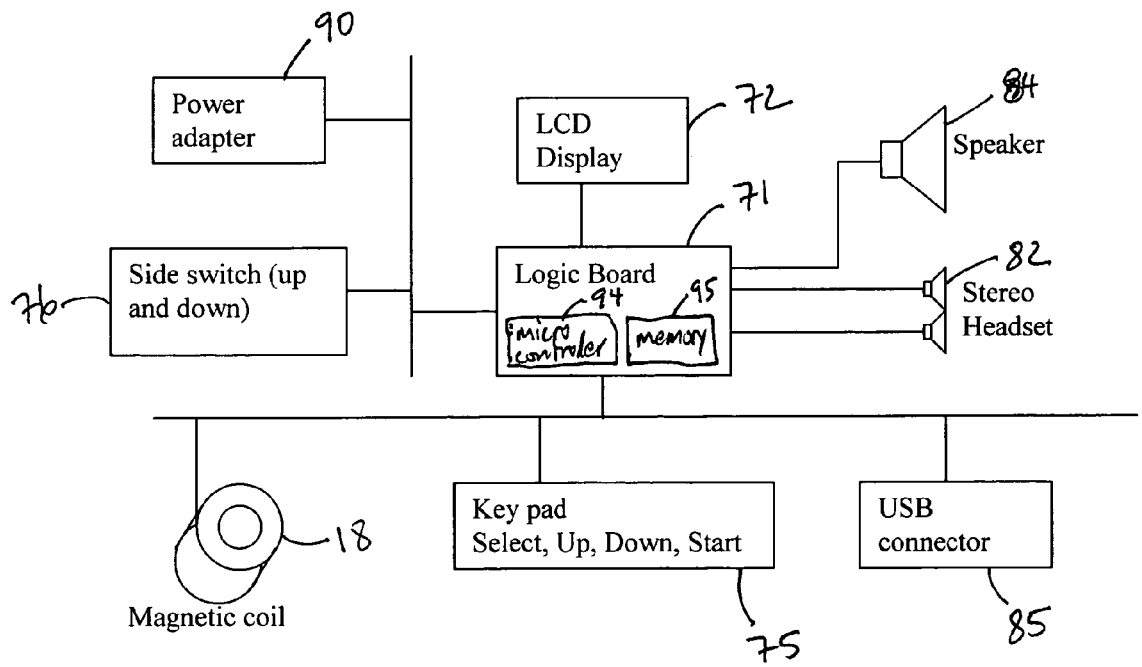
FIG. 8 is a schematic representation of a device in accordance with the present invention.

This embodiment, a schematic drawing of which is shown in FIG. 8, comprises, generally, logic board 71 for coil excitation and user control, LCD display 72, four-button function control 75, two side-of-case buttons 76 for power and menu selection, jack for stereo headset 82, integrated speaker 84, USB interface 85, power adapter 90, and software stored within memory on logic board 71.

As will be explained more fully below, this embodiment includes enhanced magnetic field control, enhanced overall control, and enhanced user benefits, as compared to the device 10. For example, as one distinct difference, device 70 preferably includes a display that displays menu/mode choices, field frequency and Time of therapy. As shown more clearly in FIG. 9, four-button function control 75 includes buttons for selecting one of the following exemplary items that would be displayed:

Brain Entrainment

Nap

Sleep

Sleep enhancing recovery and athletic performance
Sleep enhancing REM
Local Recuperation User interface buttons are also preferably provided for starting operations or for selecting up or down functions for increasing/decreasing, e.g., the volume of audio output through stereo headset 82.

USB connector 85 is preferably used to connect to a computer, portable memory card or, e.g., the Internet, to enable field upgrading of programs and for downloading audio programs. In the preferred implementation, software, upgradeable via USB connector 85 and running on logic board 71, controls the timing for coil excitation.

More detailed descriptions of the features of device 70 are set forth below.

Logic Board

Referring again to FIG. 8, logic board 71 controls the operation of device 70 and can be considered the heart of the system. It preferably comprises a microcontroller 94 along with flash memory 95. Microcontroller 94 monitors the status of the control buttons and accordingly controls the frequency of pulses for excitation of coils. Logic board 71 is also preferably configured to play audio as selected by the user. One possible variation could be to add a SD/MMC (Secure Digital/Multimedia Card) slot, so that, in addition to USB interface/connector 85, a user without a computer system can use SD/MMC for the purposes of downloading program updates and music.

LCD Display

Figure 9:
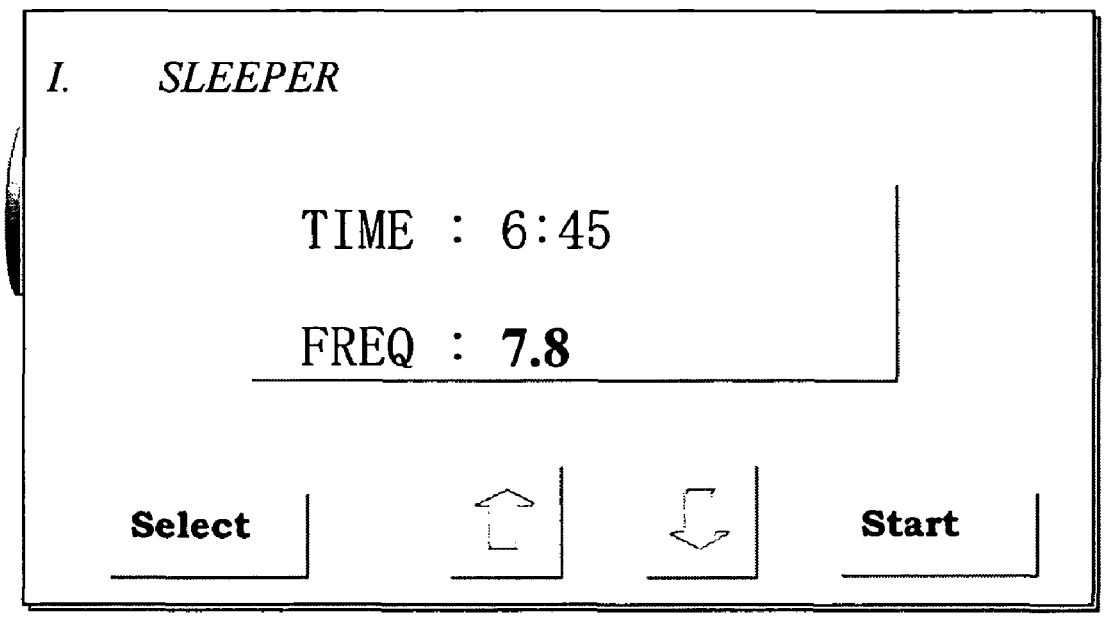
FIG. 9 is a schematic representation of the user interface of the device in accordance with the present invention.

Display 72 displays menu choices, frequency and Time of therapy as shown in FIG. 9. LCD display 72 may include graphics, color, or may be a relatively simple LED display. Menu options preferably include Mode/time (e.g., Elapsed Time/Time left) and audio.

Front Buttons for Control

Buttons 75 are used to select, or to start operations, to select up or down functions, or to increase/decrease audio volume. Buttons 75 are preferably used to select a menu option, scroll through options upward or downward, and start the selected operation. An alternative implementation might include a touch screen, with or without a stylus.

Side Buttons

Side buttons 76 may similarly be used to select up or down functions or to increase/decrease volume. Side buttons may also be used to scroll through a menu. A jog wheel, or similar mechanical device, is preferably employed for this purpose.

Modular Designed Electromagnet

An air core magnet like 18A exhibits relatively clean on-off characteristics, which are different from hard-ferrous solid core magnets with or without an outer jacket, like electromagnet 18B. The modular design of the electromagnetic coil of the present invention, another embodiment of which is shown in FIGS. 10A-C, allows a user to convert a simple air core electromagnet, to a solid-core of hard ferrous metal, resulting in a component with magnetic memory. In another embodiment a "hard" ferrous jacket may also be installed which causes the "south" polarity magnetic field to wrap from the reverse side of the magnet to a given treatment surface, thereby enhancing field gradient in the tissues being treated.

Referring to FIGS. 10A-C, there is shown a modular electromagnet that comprises a hard ferrous metal outer casing 1010 into which is disposed an inner air coil (wire coil is not shown). An outer air coil 1014 is disposed surrounding inner air coil 1012 inside outer casing 1010. Finally, a hard ferrous metal core 1016 is provided in a cavity within inner air coil 1012. FIGS. 10B and 10C show a perspective view and a partial cutaway view of the assembled modular electromagnet.

Stereo Handset

Stereo headset 82 is used for listening to stereo audio programs in privacy. Stereo headset 82 preferably emits either soothing music that contributes to a calm environment, meditation or to provide learning programs during therapy.

Speaker

Speaker 84 can be used in lieu of a headset. The stereo headset jack can also be connected to a home stereo/theatre system.

USB Interface

USB interface or connector 85 is preferably used for connecting to a computer, a memory card, or the Internet for field upgrading of programs and for downloading audio. In one implementation, USB connector 85 can be used to program device 70 to generate synchronized binaural beats and/or light therapy to the pulsed electromagnetic field. USB connector 85 may also be used for remote device diagnostics, in the event a malfunction occurs. USB connector 85 can also be used to upload user characteristics so that patient compliance issues can be addressed by the practitioner or manufacturer. Such diagnostics could occur over the Internet through a predetermined web site. Other connectivity means such as Blue Tooth, Zigbee, Wi-Fi, and the like can also serve to provide connectivity to device 70.

Software

Device 70 is preferably digitally controlled via software loaded in memory 95 on logic board 71. This software controls the timing for coil excitation, playing of music and, as previously mentioned, can be upgraded in the field.

Figure 7:
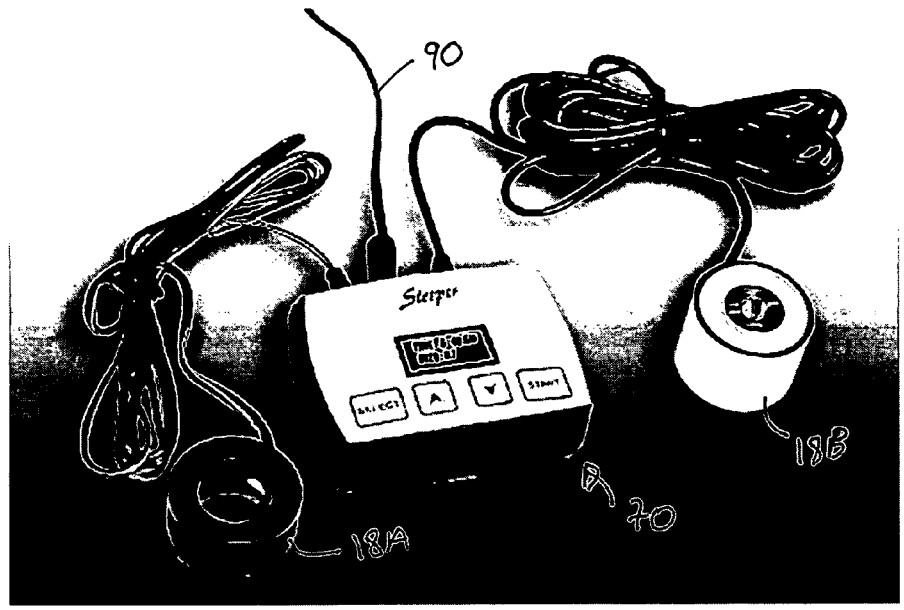
FIG. 7 is a view of a digitally-controlled with user interface device in accordance with the present invention.

As shown in FIGS. 7 and 8, logic board 71 is powered from electrical mains via power adapter 90. However, device 70 may also be operated from batteries, especially in view of the much lower power consumption resulting from an integrated package. Coil 18A/18B or a modular coil as described above, is/are connected to respective coil jack(s). Headset 82 may be connected to a headset jack.

In a preferred embodiment, the software ensures that device 70 will run a predetermined frequency sweep but over a shorter—or longer duration of time depending on a given setting on device 70. In one implementation, the unit can be set from 15 minutes to 12 hours in steps of 15 minutes. Consequently, a user has the ability to initiate a program, e.g., within 15 minutes of his desired time of wake-up. Thus, if set for 1 hour, the device cycles through a program in 1 hour; if set for 12 hours for, e.g., prolonged sleep, the device preferably cycles through a given program in 12 hours.

An exemplary frequency program is as follows. If the time is set for 1 hour, the Frequency sweeps from 9.6 Hz to 0.5 Hz within 3.75 minutes in steps of 0.1 Hz. Then the frequency alternates between 0.5 Hz and 5 Hz every 3.75 minutes in steps of 0.1 Hz until total elapsed time is 45 minutes (75% complete). Then, the frequency sweeps from 5 Hz to 14.1 Hz in steps of 0.1 Hz. It is of note that 14.1 Hz is one of the predominant Schumann wave frequencies and is an alert active thought process brain wave rhythm which should allow the user to awaken in an alert, refreshed state of mind.

Of course, other programming methodologies are possible, especially in view of the ability to upgrade and modify the software in the field.

More specifically, the digitally-controlled system of the present invention might be programmed to operate at night to balance the electromagnetic fields in the body and brain. Through the concept of brain entrainment or, alternatively, through frequency specific blocking, device 70 can be programmed to sweep through a range of sleep frequencies during the night, smoothing out electromagnetic anomalies while a person is unconsciously sleeping, and thereby subsequently further "upregulating" physical and mental capabilities during the following day. Device 70 can be, for example, tuned to meditation, relaxation, or to put someone to sleep for a nap or all night, in accordance with the mode selected. Alternatively, device 70 may be tuned to "alert" frequencies for daytime use to enhance mental thought process and keep a person in active thought process mode without excess coffee or other nutritive stimulants.

Additionally, it is believed that that even faster healing occurs when a frequency, particularly 9.6 Hz (identified as creating profound analgesic and healing effects), is modulated from 9.1 to 10.1 Hz continually during a treatment session for physiological healing effects.

Studies show that brainwave anomalies in Theta rhythm occur in central nervous system disorders including ADD, migraine headaches, and like disorders. The system of the present invention preferably sweeps the theta region continually all night in 0.1 Hz steps during a nap or while sleeping cycling through REM mode several times during the night.

In each mode, e.g., brain entrainment, nap, sleep, alert, recuperation, device 70 outputs a waveform consistent with pre-programmed timings. These timings and modes are modifiable in the field through company website or memory card.

In a preferred embodiment, device 70/logic board 71 has a built-in security code to ensure that only an authorized website or memory card can modify the timings. On the other hand, audio programs are preferably downloadable without restriction, as long as the format is compatible with device 70. The MP3 format is one such format.

As mentioned previously, device 70 is preferably configured to play music. In one implementation, the software operates to play music in coordination with the particular pulse frequency. This can further enhance the therapeutic effects of the system, especially in connection with sleep and/or resting modes. However, coordinated music is not a requirement of the invention. In the case where the device is connected through the Internet, both music and associated pulse patterns can be downloaded and selected for "playback" by a user.

Continuing research with coils 18A and 18B has resulted in the discovery that these coils can produce peak electromagnetic force (PEMF) up to 30 Gauss and 90 Gauss, respectively, when not penetrating through a barrier, such as a standard 6-10 inch thick mattress.

In still further research, it has been discovered that sleeping with a solid core electromagnet generating 90 gauss and attached to a headboard of a bed 1-2 inches directly above the 'crown' of a user's head results in remarkably deep and restful sleep. Further, sleep, strength, stamina, and general focus all appear to further improve with peak EMF at levels as high as 1000 gauss. These higher levels of EMF can be attenuated as desired through, e.g., a mattress, to produce PEMF in the range substantially of 0 Gauss to 25 Gauss.

Other Embodiments

Battery Powered Medallion

Due to the size reduction and energy efficiency resulting from the SOC technology described herein, device 70 can, alternatively, be fashioned into a wearable power source and coil in the form of a medallion, as shown in FIGS. 11A-D. As shown, medallion 1100 comprises a wire coil wound around form 1110 and encased in a cover 1115. A battery 1120 and microchip 1125 are preferably secured to opposite sides of the coil, or where space is available. Medallion 1100 is preferably configured to include a rechargeable battery that could be recharged at night. The device itself can then be worn all day, using, e.g., a necklace, to neutralize the detrimental effects of man-made EMF and to help the wearer maintain an alert, focused state and reduce psychological and environmental stressors by producing a close field source of VLF magnetic fields.

Sweeping across frequencies between 10 and 14.1. Hz, the wearer's alertness is maintained. At the same time, the wearer's biological system is shielded from stressors. In particular, such frequencies may protect the wearer from detrimental effects of man-made electromagnetic pollution from, e.g., cell phones and wireless networks which create havoc to the neurological and physiological system, by creating a close source of friendly electromagnetic energy of natural endogenous and exogenous frequencies conducive to active thought process state (e.g., low beta and high alpha ranges), thereby drowning out the electromagnetic pollution of considerably higher frequencies including power frequency, radio and microwaves.

The instant medallion embodiment can also be worn over the heart for stimulation of the heart muscle, or over liver, kidneys, bone disorder, fracture or other tissue, which is failing in health. Medallion 1100 can be placed on the body in the appropriate position by fastening with tape, Velcro or straps. The device can be worn by a user for up to 8-16 hours per day due to variable frequency and very low amplitude.

More specifically, as shown in FIGS. 12A-D, medallion 1100 can be secured in a pouch 1200 that preferably includes a belt loop 1210 through which a belt can be passed and then fastened to the user. FIG. 12A is a front view with medallion 1100 being inserted into pouch 1200 and FIG. 12B is a front view of the pouch. FIG. 12C shows belt loop 1210 and a flap 1220 that can be secured via a hook and loop fastener pair 1240. A belt could be a weight-lifting type belt, or a back-brace 1300, as shown in FIG. 13, to have dual advantage of reducing weight upon the lower back structure and maintaining better disk alignment and posture, while PEMF goes to work enhancing blood flow, relaxing muscles, regenerating damaged bone, cartilage, ligament and nerve tissue.

Far Infrared/Pulsed far Infrared

The features of the present invention may also be combined with far infrared heat for synergistic effects. Research has determined that addition of radiant or far infrared heating pad to physiological therapy applications synergistically affect the therapeutic outcome, therefore an apparatus for generating continuous or pulsed infrared heat could be combined with the weight-lifting type fixation belt and PEMF concentric circle coil described above. This combination is proving to be particularly effective with respect to sever lower back pain symptoms.

Medallion For Helmet Retrofit

More stable and reliable neurological entrainment and stimulation can be achieved by adapting the medallion style device to be incorporated into a helmet, as shown in FIGS. 14A and 14B, for use in military, auto racing or any sport/activity which normally requires high degree of concentration over long periods of time, especially where fatigue and stress can be problematic. In the case of FIG. 14A, the medallion style device is inserted into padding 1410 of helmet 1400, whereas in FIG. 14B, a pouch-like device, like pouch 1200, is used to attach the device to internal webbing 1420 of helmet 1400. In a military application, troops in the field will be able to maintain focus and reduce stress in face of combat fatigue by utilizing the device in high alpha-low beta range during day. When the time arrives for napping or sleeping, the device can be tuned to promote relaxation, which is more conducive to sleeping and physical recuperation. More importantly, while the user sleeps, the body is in more recuperative state than normal so that one can maintain effectiveness on substantially less sleep and repair normal wear and tear by substantially more effective means.

As enhanced strength, stamina and motor coordination are all routinely upregulated by the device, soldiers wearing the device will be more effective in situations of hand to hand combat and others where strength to weight ratio are important.

Medallion for Bone Stimulation and Tumor Treatment

A medallion device consistent with the present invention can also be positioned in proximity to a fracture or bone non-union on the outside of a cast or fixation device.

Further, as it is being discovered more and more that cancer cells do not propagate well within a North Pole field (because they themselves carry a South Pole field) the medallion or the other configurations described herein can be worn in proximity to a user's known cancerous tumors.

Smart Home Application

Devices in accordance with the present invention can also be configured to be plugged directly into any electrical wall outlet or even hardwired into a home to create a home network whereby the devices are controlled by the home's computer or set individually in each room according to a user's preferences. Preferably the device creates a frequency 'zone' in any room that overshadows any other EMF present in that room. As an example, a bedroom can be tuned to a relaxed state at night, and an alert state in the morning whereas an office can be tuned to alert frequencies 24 hours per day.

Automobile Application

As the detrimental effects of EMF become more well-known, it will be found that one of the most detrimental EMF spaces are those in an automobile. These EMF's are concentrated forward of the passenger compartment putting the driver and his front seat passenger in proximity to the largest fields. The device of the present invention can be configured to be powered from a cigarette lighter and to direct North Pole energy into the passenger compartment. The device may also be programmed to scan the 'alert' state frequencies whenever plugged in, and thereby help to maintain a driver's alert state.

Agriculture

The frequencies and EMF magnitudes described herein have been used successfully to improve the growth rate and taste of various fruits and vegetables in a small garden setting with electromagnetic field generating coils spaced throughout a small plot of vegetables and fruits. With only a negligible increase in electric consumption, the average home gardener may experience an increased yield of up to 20% per square meter of garden which will yield tastier and perhaps more nutritious fruits and vegetables.

Aquaculture

In a similar way to the agriculture application, exposing hatchlings to the electromagnetic energy described herein may also be used to enhance growth rate, thereby. Hatchlings could be in tanks or small ponds into which the EMF can be directed significantly reducing the time required before harvesting.

PEMF Used Synergistically with Silver Ion Wound Dressings

It is now well established that a silver ion wound dressing is bacteriostatically superior to all other wound care therapies. What is proposed herein is the novel synergistic use of extremely low frequency, pulsed North pole/South pole concentric circle application of electromagnetic energy at 100-1000 gauss, using an 8 hours on/8 hours off cycle, although other timing cycles or electromagnet configurations such as air-core or medallion embodiments could be employed. This energy is preferably applied through moistened silver nylon bandages with or without use of microampere negative D.C. electric currents.

While the invention has been described with reference to a preferred embodiment, it should be understood by those skilled in the art that various changes may be made and equivalents substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for generating frequencies related to sleep and alert states, comprising:
    a circuit configured to produce, at an output of the circuit, a pulsed DC signal having a frequency, wherein the frequency falls within a range of brain wave frequencies that includes a plurality of segments, the plurality of segments including a delta segment, a theta segment, an alpha segment and a beta segment, each of the delta, theta, alpha and beta segments corresponding to a respective subrange of the brain wave frequencies;
    a frequency controller, coupled to the circuit, configured to change the frequency of the pulsed DC signal from a first frequency to a second frequency,
        wherein the second frequency is within a second one of the plurality of segments, and
        wherein the first frequency is a non-zero frequency outside of the second one of the plurality of segments; and
    a coil, coupled to the output of the circuit, configured to generate a magnetic field from the pulsed DC signal.

2. The apparatus of claim 1, wherein the coil is configured to generate a magnetic field having a first magnetic field component with a first polarity and a second magnetic field component with a second polarity, the first polarity being opposite of the second polarity, the first magnetic field component varying in time, the second magnetic field component being substantially static in time and extending generally concentric to the first magnetic field component.

3. The apparatus of claim 1, wherein the delta segment includes frequencies in a range of about 0 to 3 Hz, wherein the theta segment includes frequencies in a range of about 3 Hz to about 8 Hz, wherein the alpha segment includes frequencies in a range of about 8 Hz to about 12 Hz and wherein the beta segment includes frequencies in a range of about 12 Hz and higher.

4. The apparatus of claim 1, wherein the second one of the plurality of segments is the delta segment.

5. The apparatus of claim 1, wherein the first frequency is within the range of brain wave frequencies.

6. The apparatus of claim 5, wherein the first frequency is within a first one of the plurality of segments.

7. The apparatus of claim 6, wherein the first one of the plurality of segments is the delta segment.

8. The apparatus of claim 1, wherein the coil is adapted to be positioned beneath a sleeping surface of a patient and operative to direct the magnetic field to the patient.

9. The apparatus of claim 1, wherein, upon changing the frequency of the pulsed DC signal from the first frequency to the first second frequency, the frequency controller is further configured to substantially maintain the frequency of the pulsed DC signal at the second frequency for a second time interval.

10. The apparatus of claim 5, wherein the frequency controller is further configured to substantially maintain the frequency of the pulsed DC signal at the first frequency for a first time interval, and upon changing the frequency of the pulsed DC signal to the second frequency, substantially maintain the frequency of the pulsed DC signal at the second frequency for a second time interval.

11. The apparatus of claim 10, wherein the frequency controller is further configured to shift the frequency of the pulsed DC signal from the second frequency to a third frequency and to substantially maintain the frequency of the pulsed DC signal at the third frequency for a third time interval.

12. An apparatus for generating frequencies related to sleep and alert states, comprising:
a circuit configured to produce, at an output of the circuit, a pulsed DC signal having a frequency, wherein the frequency falls within a range of brain wave frequencies that includes a plurality of segments, the plurality of segments including a delta segment, a theta segment, an alpha segment and a beta segment, each of the delta, theta, alpha and beta segments corresponding to a respective subrange of the brain wave frequencies;
a frequency controller, coupled to the circuit, configured to incrementally change the frequency of the pulsed DC signal from a first frequency to a second frequency in frequency steps over a time interval,
wherein the first frequency is within a first one of the plurality of segments, and
wherein the second frequency is within a second one of the plurality of segments; and
a coil, coupled to the output of the circuit, configured to generate a magnetic field from the pulsed DC signal.

13. The apparatus of claim 12, wherein the coil is configured to generate a magnetic field having a first magnetic field component with a first polarity and a second magnetic field component with a second polarity, the first polarity being opposite of the second polarity, the first magnetic field component varying in time, the second magnetic field component being substantially static in time and extending generally concentric to the first magnetic field component.

14. The apparatus of claim 12, wherein the delta segment includes frequencies in a range of about 0 to 3 Hz, wherein the theta segment includes frequencies in a range of about 3 Hz to about 8 Hz, wherein the alpha segment includes frequencies in a range of about 8 Hz to about 12 Hz and wherein the beta segment includes frequencies in a range of about 12 Hz and higher.

15. The apparatus of claim 12, wherein the first one of the plurality of segments is the delta segment.

16. The apparatus of claim 12, wherein the second one of the plurality of segments is the delta segment.

17. The apparatus of claim 12, wherein the frequency controller is further configured to substantially maintain the frequency of the pulsed DC signal at the first frequency for a first time interval and to substantially maintain the frequency of the pulsed DC signal at the second frequency for a second time interval.

18. The apparatus of claim 12, wherein the frequency controller is further configured to incrementally change the frequency of the pulsed DC signal from the second frequency to a third frequency.

19. The apparatus of claim 17, wherein the frequency controller is further configured to incrementally change the frequency of the pulsed DC signal from the second frequency to a third frequency and to substantially maintain the frequency of the pulsed DC signal at the third frequency for a third time interval.

20. An apparatus for generating magnetic fields related to sleep and alert states for application to a patient, comprising:
a circuit configured to produce a pulsed DC signal at an output of the circuit, the signal having a frequency characteristic;
a coil, coupled to the output of the circuit, configured to generate a magnetic field from the signal,
a controller, coupled to the circuit, configured to:
cause the circuit to generate the signal such that the frequency characteristic of the signal begins at a first frequency comprising an alpha brainwave frequency, and
lower the frequency characteristic of the signal to at least a second frequency comprising a delta brainwave frequency.

21. The apparatus of claim 20, wherein the controller configured to lower the frequency characteristic of the signal to at least a second frequency is further configured to lower the frequency characteristic through one or more additional frequencies between the first frequency and the at least a second frequency.

22. The apparatus of claim 21, wherein at least one of the one or more additional frequencies comprises a theta brainwave frequency.

23. The apparatus of claim 20, wherein the controller configured to lower the frequency characteristic of the signal to at least a second frequency is further configured to sweep the frequency characteristic through a plurality of additional frequencies between the first frequency and the at least a second frequency in 0.1 Hz increments.

24. The apparatus of claim 20, wherein the alpha brainwave frequency is within the range of about 8 to 12 Hz.

25. The apparatus of claim 20, wherein the delta brainwave frequency is within the range of about 0 to 3 Hz.

26. The apparatus of claim 22, wherein the theta brainwave frequency is within the range of about 3 to 8 Hz.

27. A method for generating magnetic fields relating to sleep and alert states for application to a patient, comprising:
causing a circuit to produce a pulsed DC signal, the signal having a frequency characteristic, wherein a coil, coupled to an output of the circuit generates a magnetic field from the signal, and wherein the frequency characteristic of the signal begins at a first frequency comprising an alpha brainwave frequency;
lowering the frequency characteristic of the signal to at least a second frequency comprising a delta brainwave frequency.

28. The method of claim 27, wherein lowering the frequency characteristic of the signal to at least a second frequency comprises lowering the frequency characteristic through one or more additional frequencies between the first frequency and the at least a second frequency.

29. The method of claim 28, wherein at least one of the one or more additional frequencies comprises a theta brainwave frequency.

30. The method of claim 27, wherein lowering the frequency characteristic of the signal to at least a second frequency comprises sweeping the frequency characteristic through a plurality of additional frequencies between the first frequency and the at least a second frequency in 0.1 Hz increments.

31. The method of claim 27, wherein the alpha brainwave frequency is within the range of about 8 to 12 Hz.

32. The method of claim 27, wherein the delta brainwave frequency is within the range of about 0 to 3 Hz.

33. The method of claim 29, wherein the theta brainwave frequency is within the range of about 3 to 8 Hz.

* * * * *